United States Patent
Liu et al.

(10) Patent No.: US 12,110,542 B2
(45) Date of Patent: Oct. 8, 2024

(54) ISOTHERMAL AMPLIFICATION

(71) Applicant: University of Connecticut, Farmington, CT (US)

(72) Inventors: Changchun Liu, Farmington, CT (US); Xiong Ding, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 141 days.

(21) Appl. No.: 17/472,300

(22) Filed: Sep. 10, 2021

(65) Prior Publication Data

US 2022/0081712 A1 Mar. 17, 2022

Related U.S. Application Data

(60) Provisional application No. 63/076,451, filed on Sep. 10, 2020.

(51) Int. Cl.
*C12Q 1/6855* (2018.01)

(52) U.S. Cl.
CPC .................................. *C12Q 1/6855* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 6,410,278 B1 | 6/2002 | Notomi et al. | |
| 8,017,357 B2 * | 9/2011 | Notomi | C12Q 1/6844 435/6.12 |
| 2021/0238667 A1 * | 8/2021 | Georgiou | C12Q 1/6858 |

OTHER PUBLICATIONS

Ding, Dual-Priming Isothermal Amplification (DAMP) for Highly Sensitive and Specific Molecular Detection with Ultralow Nonspecific Signals, Anal. Chem., 91, 12852-12858, 2019. (Year: 2019).*
Nagamine, Accelerated reaction by loop-mediated isothermal amplification using loop primers, Molecular and Cellular Probes, 16, 223-229, 2002. (Year: 2002).*
Van Pelt-Verkuil et al., "PCR Primers", in Principles and Technical Aspects of PCR Amplification, Springer Science + Business Media B.V., 2008. (Year: 2008).*
ANONYMOUS; "PrimerExplorer V4: A Guide to LAMP primer designing"; Eiken Chemical Co., LTD; Manual No. 1; available online at https://primerexplorer.jp/e/v4_manual/pdf/PrimerExplorerV4_Manual_1.pdf [retrieved Sep. 10, 2021]; 2009; 18 pages.
Gabrielle, M. et al.; "Nucleic acid sequence-based amplification (NASBA) for the identification of mycobacteria"; Journal of General Microbiology, vol. 139; 1993; pp. 2423-2429.
Mok, E. et al.; "Comprehensive evaluation of molecular enhancers of the isothermal exponential amplification reaction"; Scientific Reports, vol. 6; Article No. 37837; 2016; 10 pages; https://doi.org/10.1038/srep37837.
Yang, L. et al.; "Critical Role of Magnesium Ions in DNA Polymerase β's Closing and Active Site Assembly"; Journal of the American Chemical Society, vol. 126; 2004; pp. 8441-8453.

* cited by examiner

*Primary Examiner* — Angela M. Bertagna
*Assistant Examiner* — Carolyn L Greene
(74) *Attorney, Agent, or Firm* — CANTOR COLBURN LLP

(57) ABSTRACT

Disclosed herein are "dual-priming" isothermal amplification method (including "self-priming" and "pairing-priming" strand extension, termed "DAMP") for rapid nucleic acid detection.

6 Claims, 23 Drawing Sheets

Specification includes a Sequence Listing.

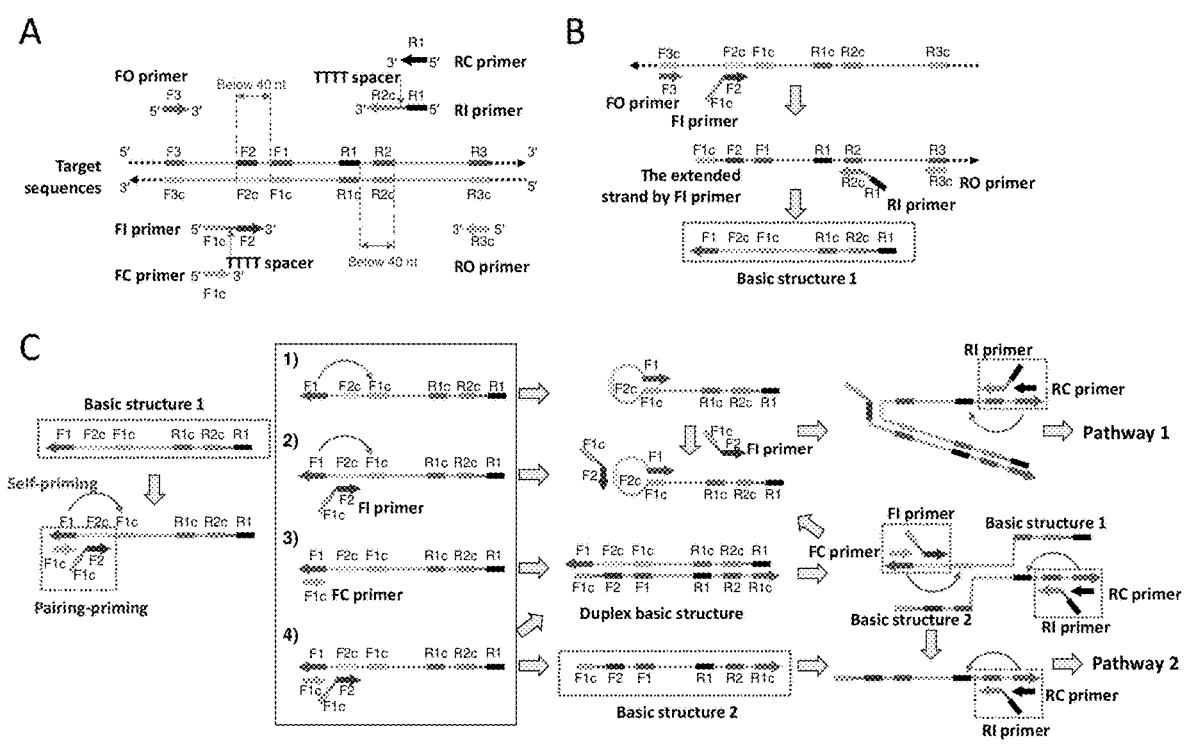
FIG. 1A-C

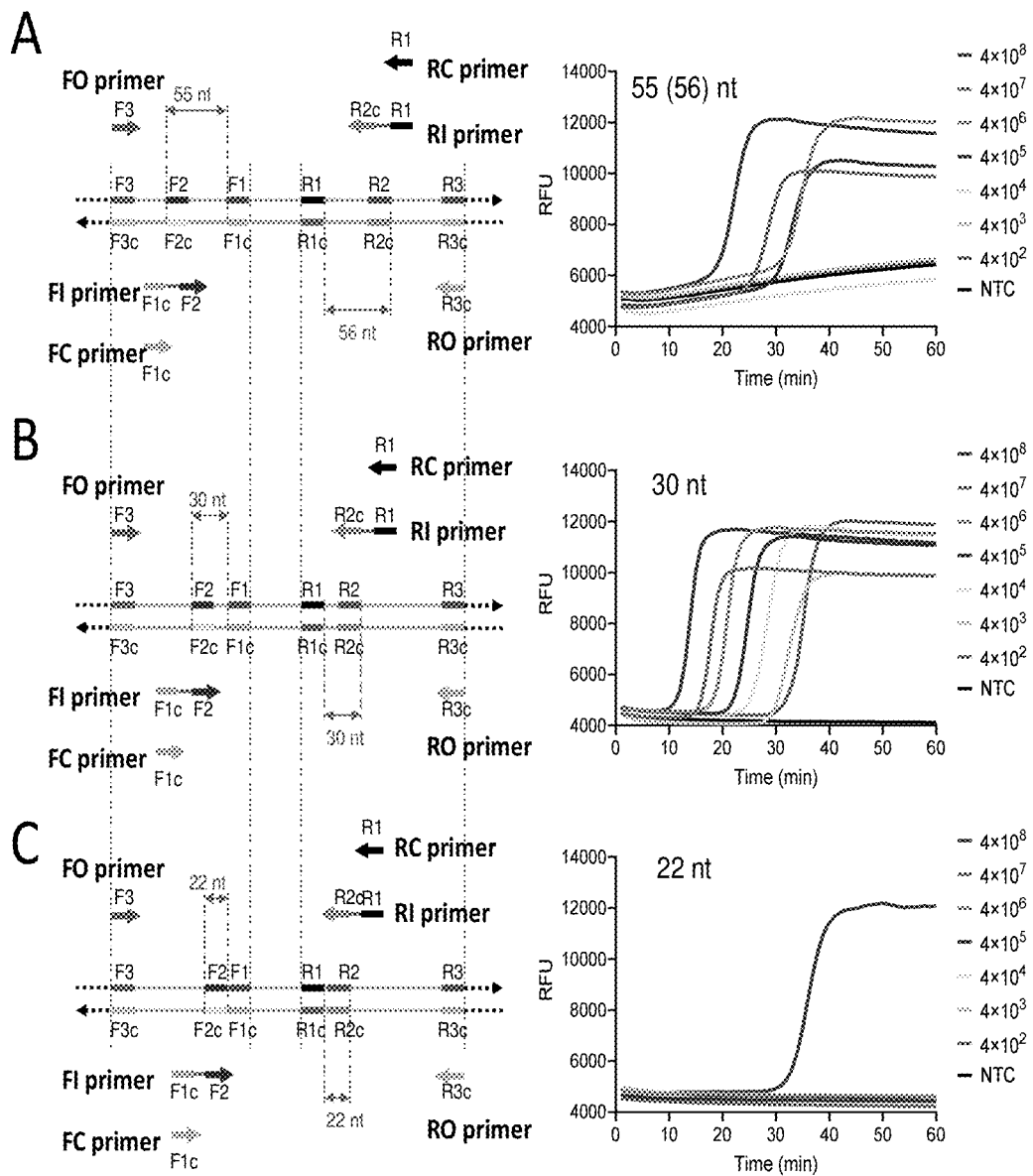
FIG. 2A-C

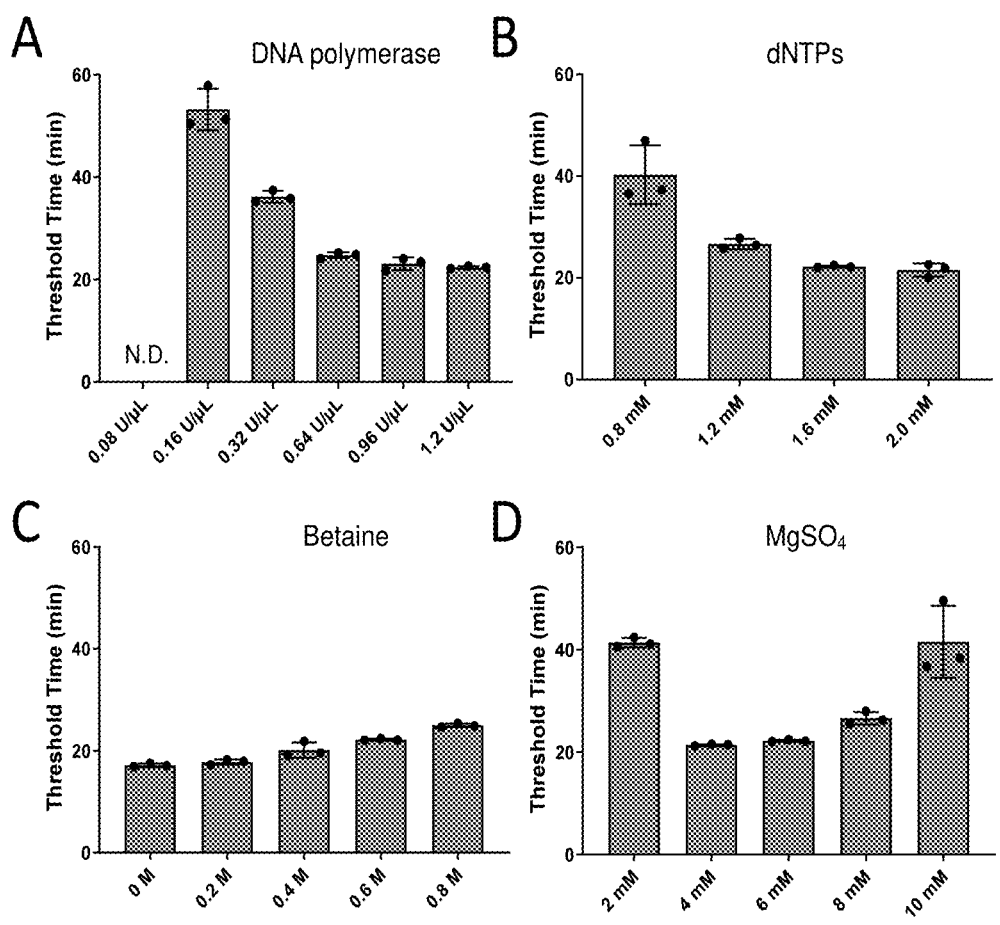
FIG. 3A-D

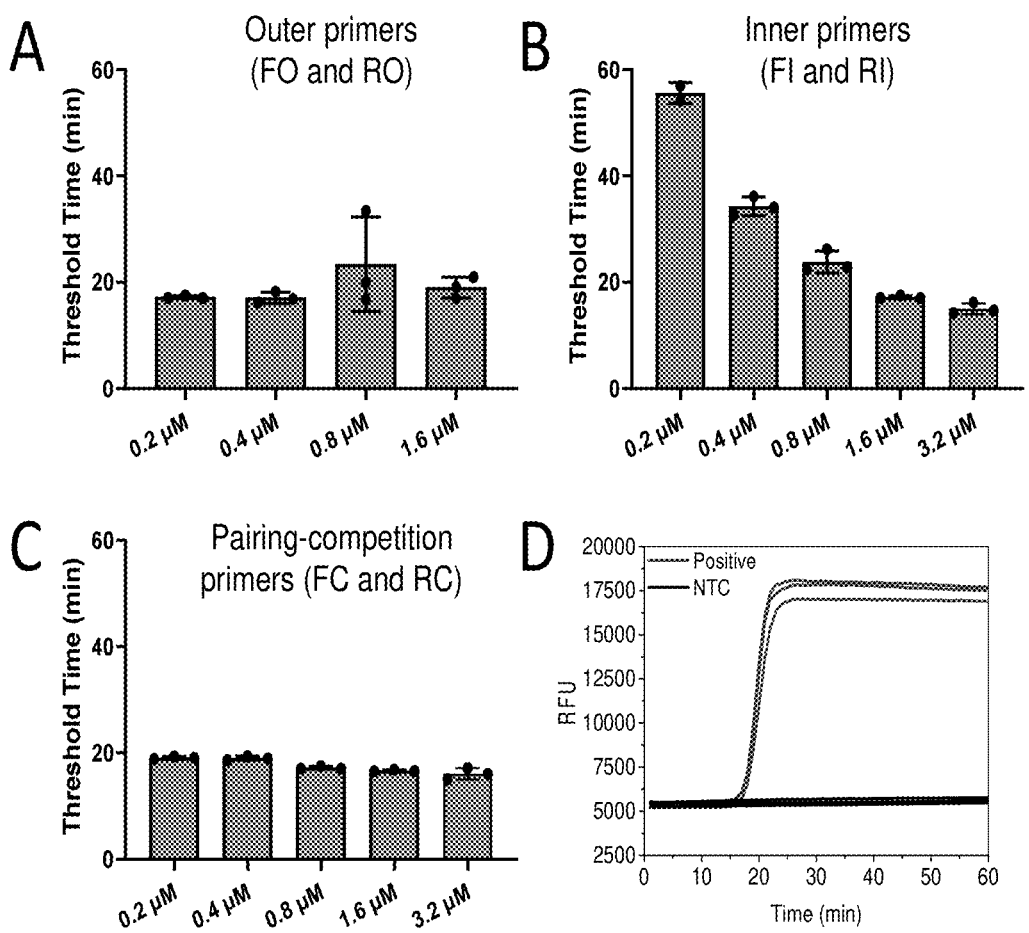
FIG. 4A-D

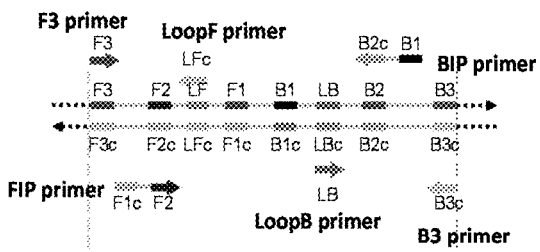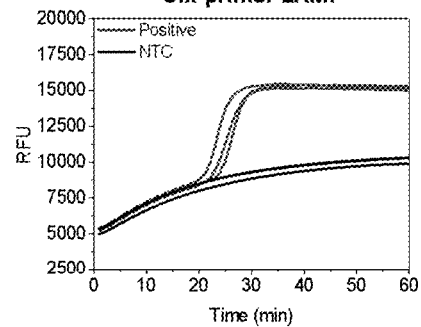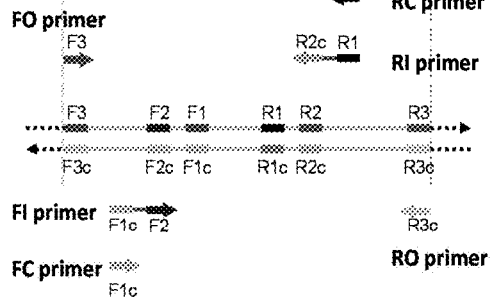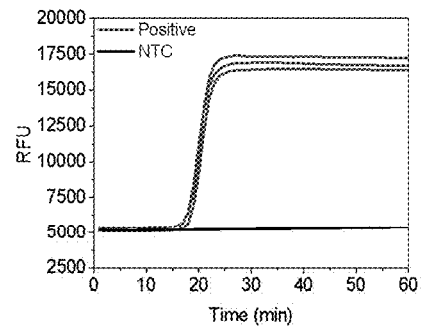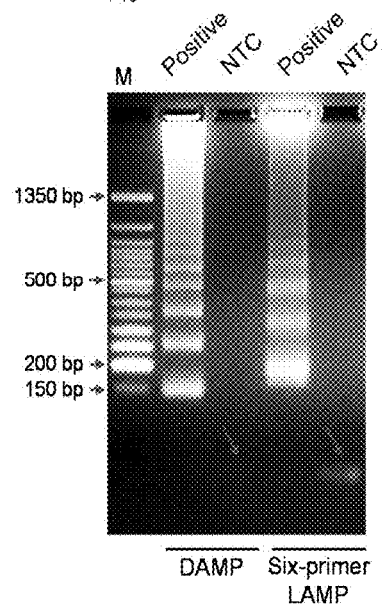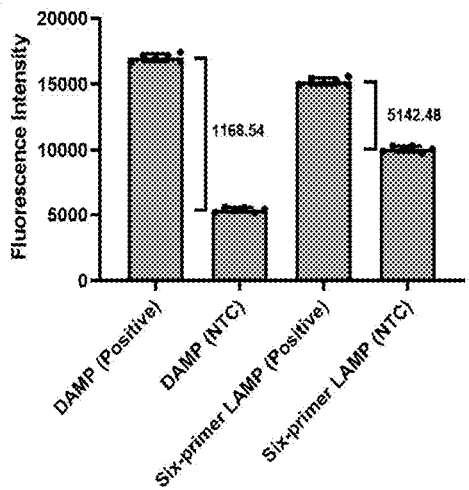
FIG. 5A-D

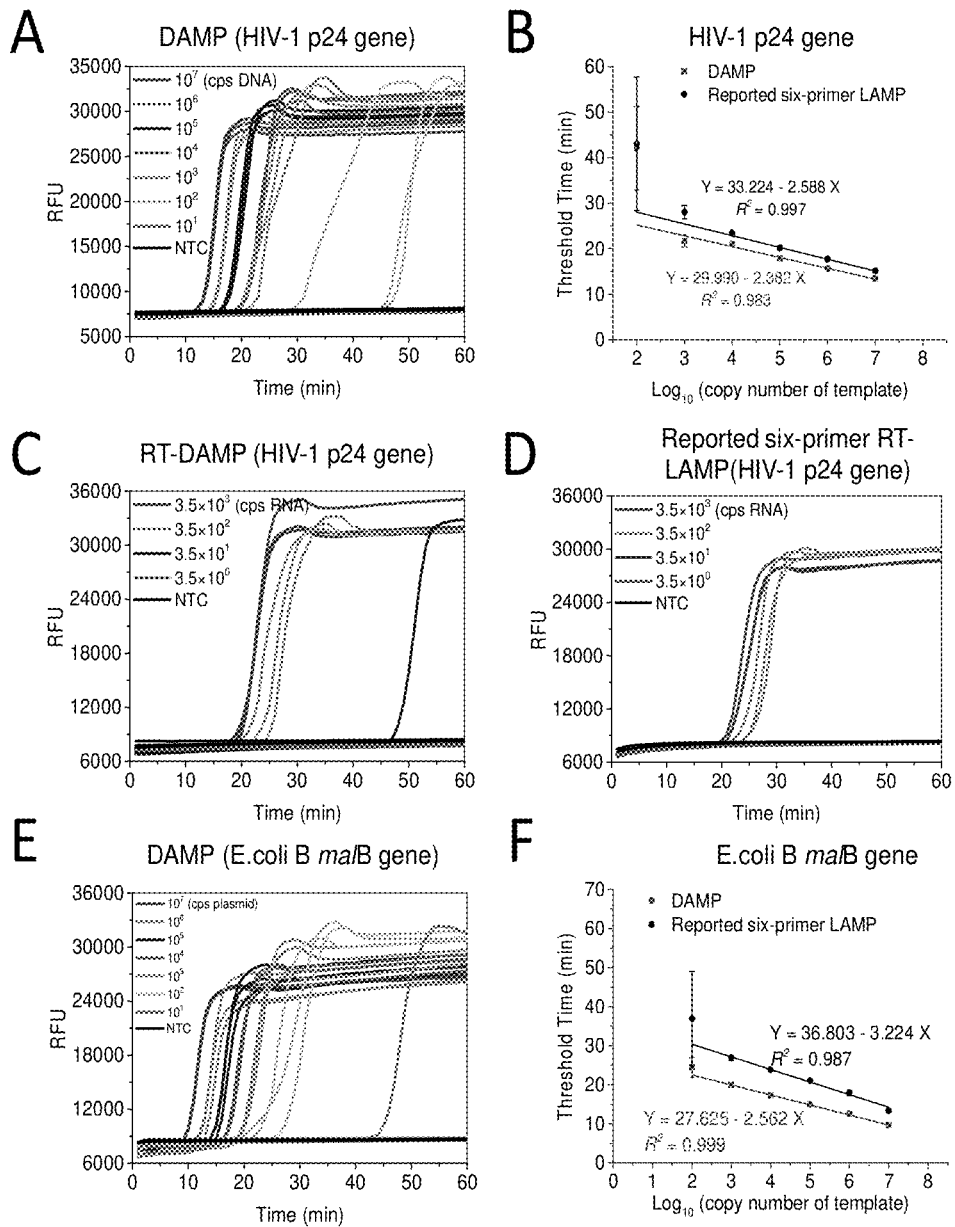
FIG. 6A-F

A
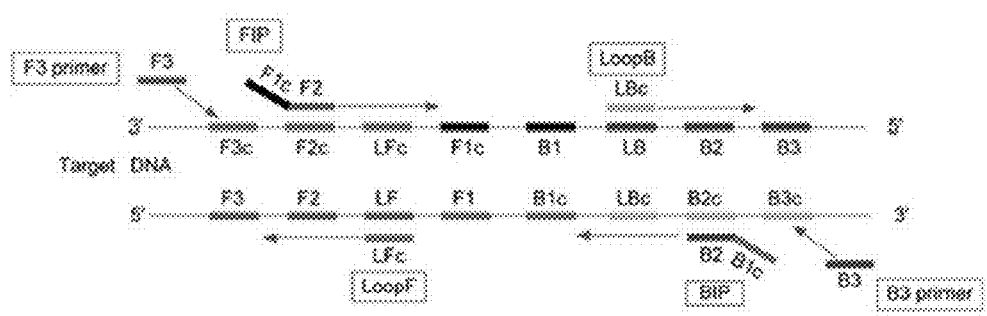
B
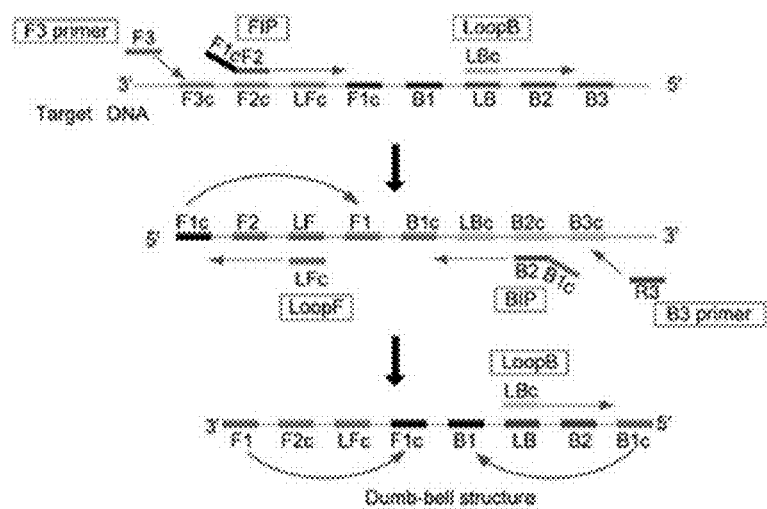
FIG. 7A-B

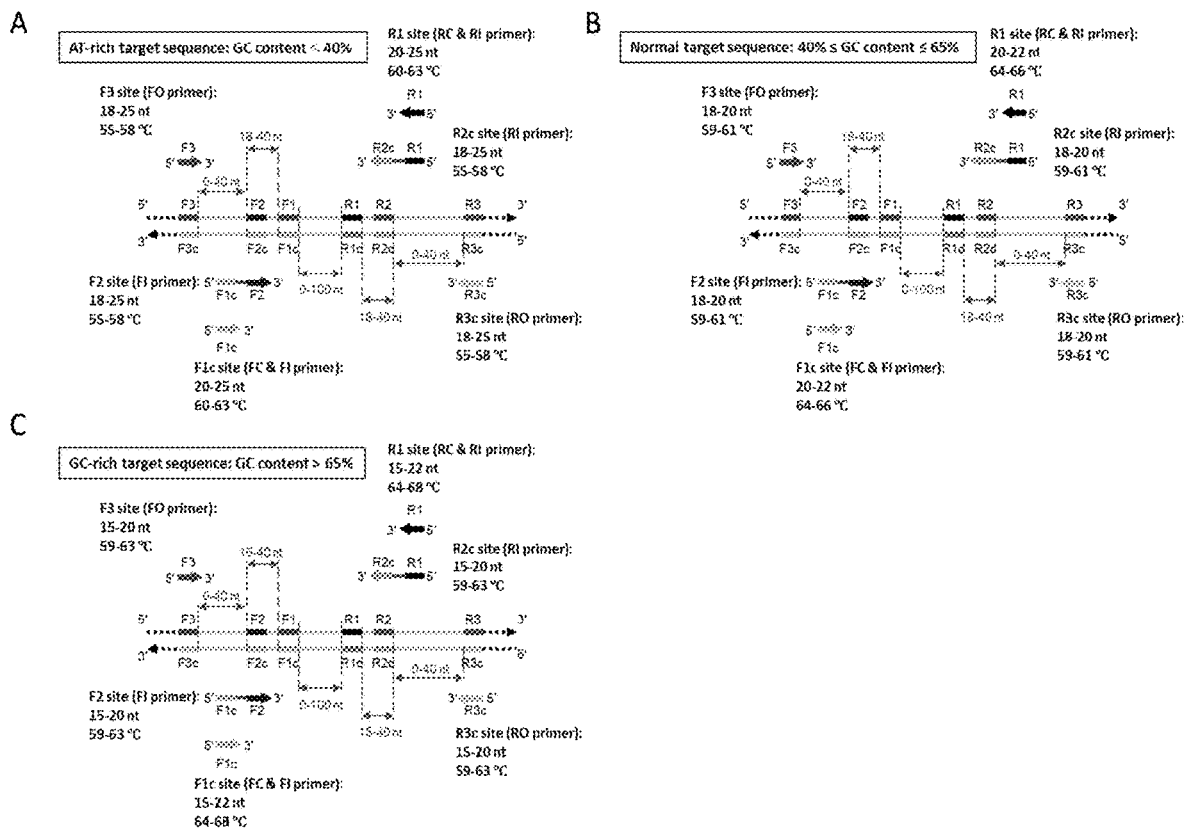
FIG. 8A-C

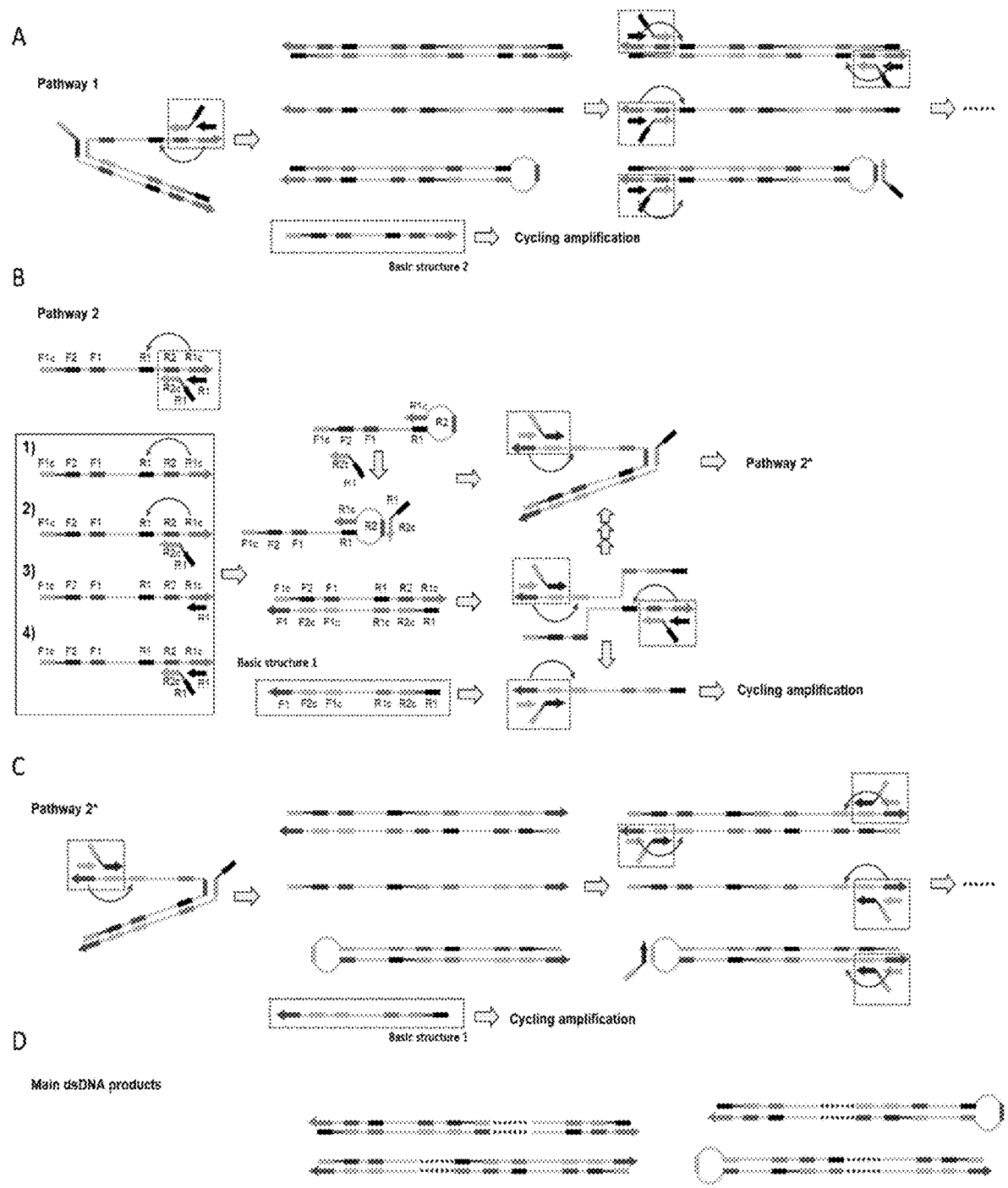
FIG. 9A-D

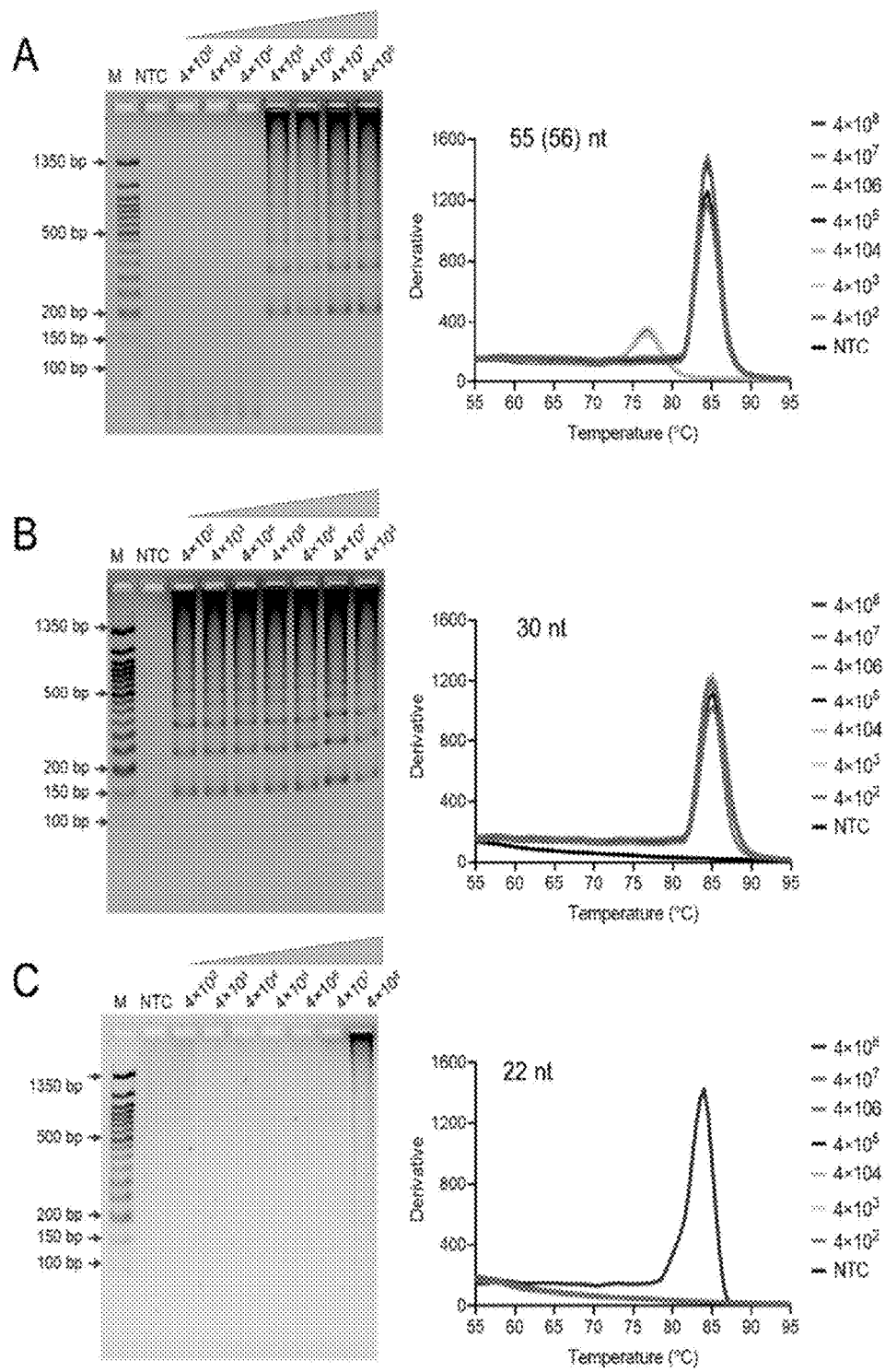
FIG. 10A-C

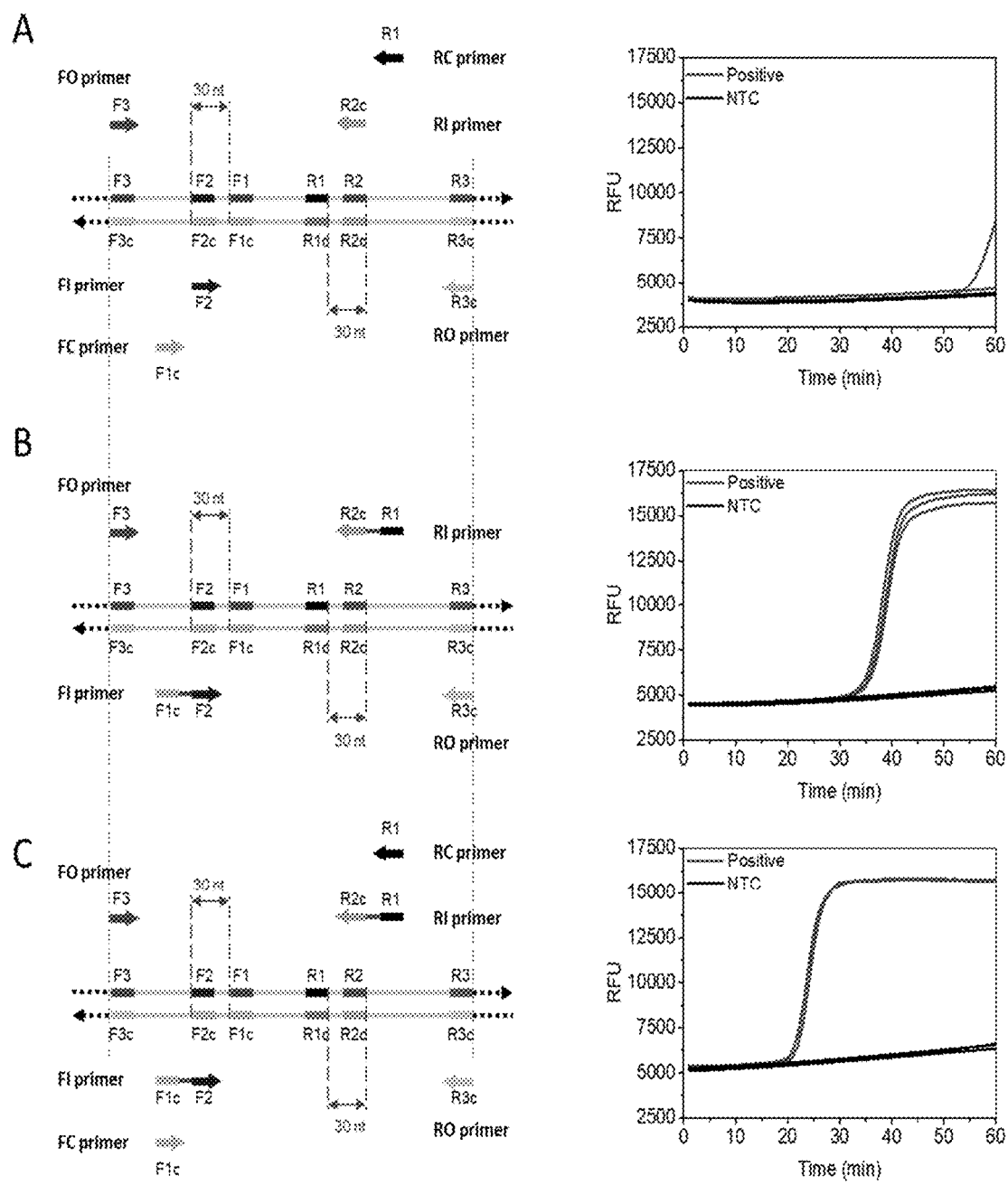
FIG. 11A-C

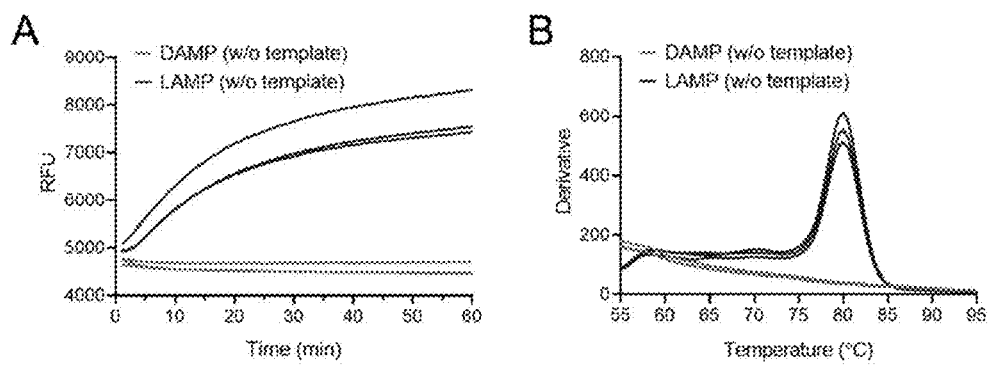
FIG. 19A-B
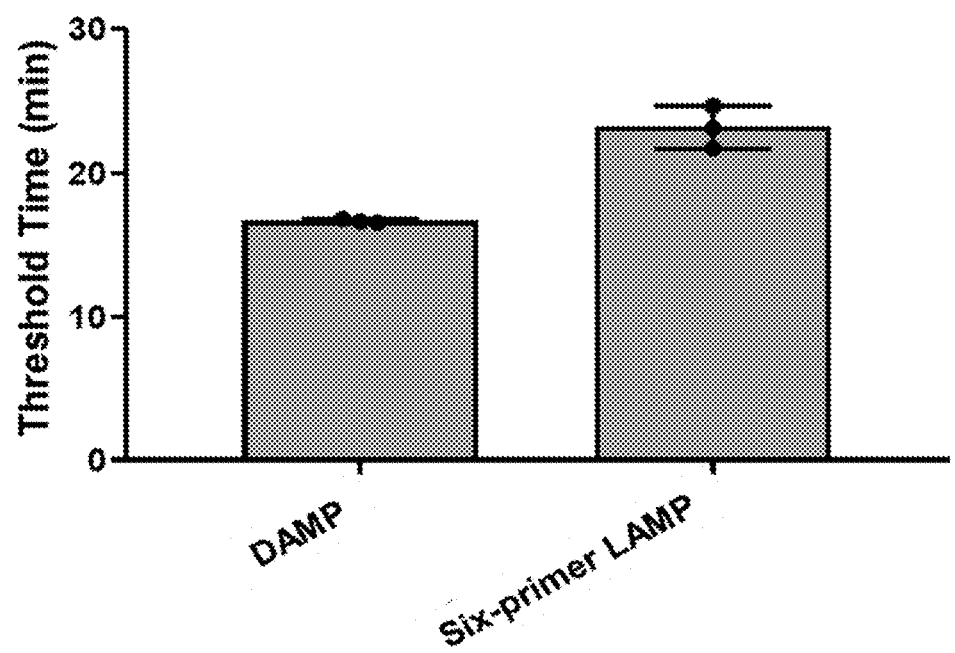
FIG. 20

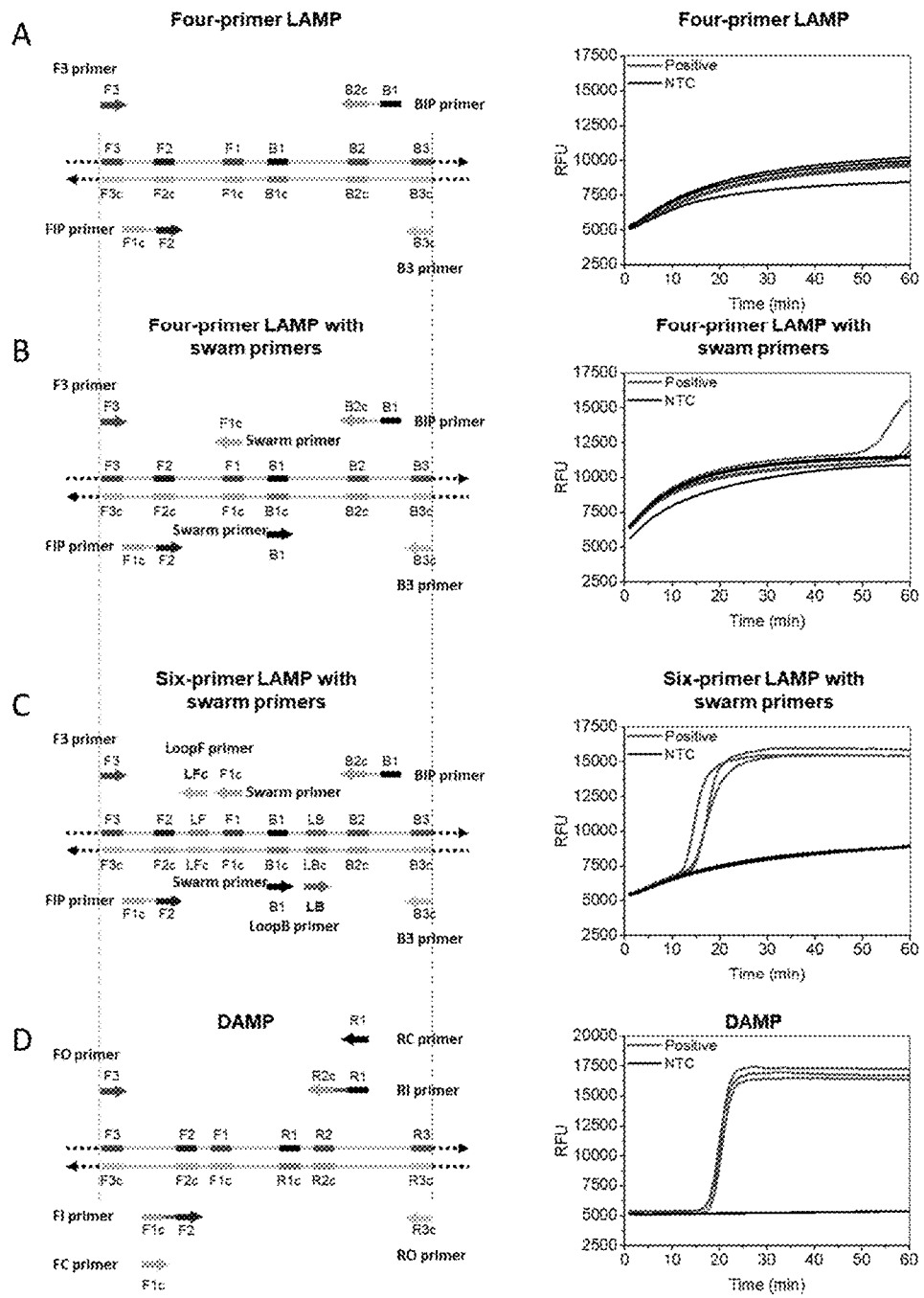
FIG. 21A-D

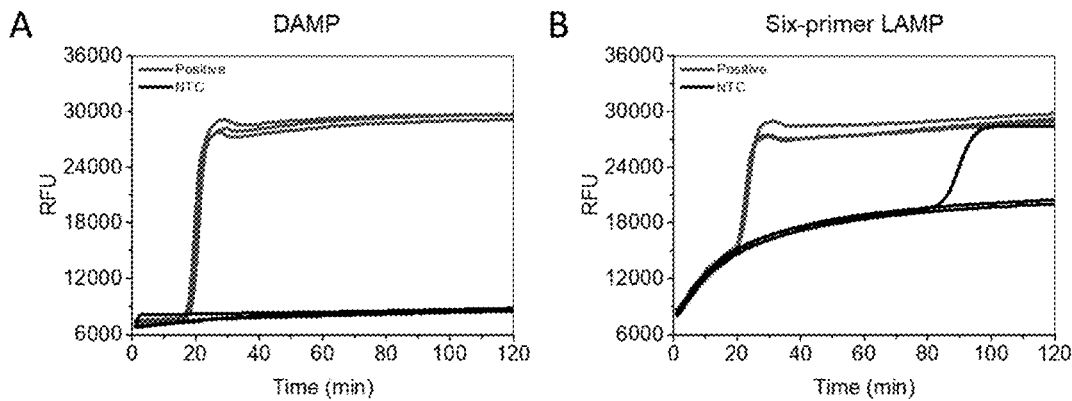
FIG. 22A-B
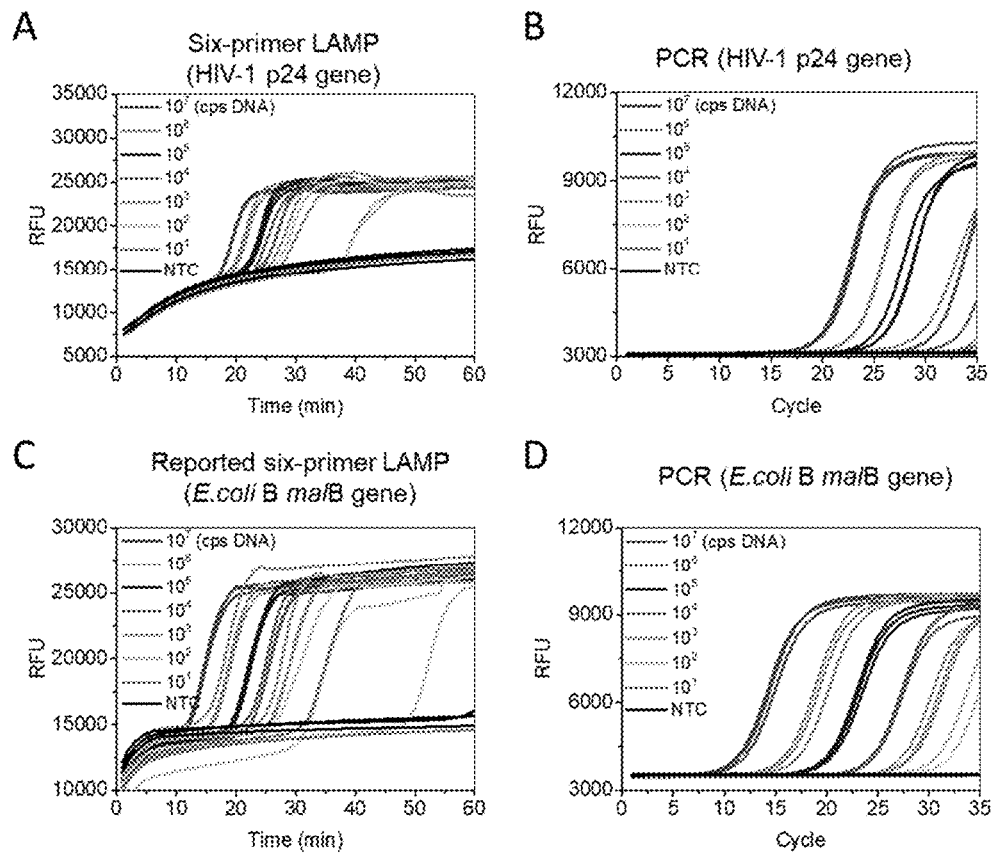
FIG. 23A-D

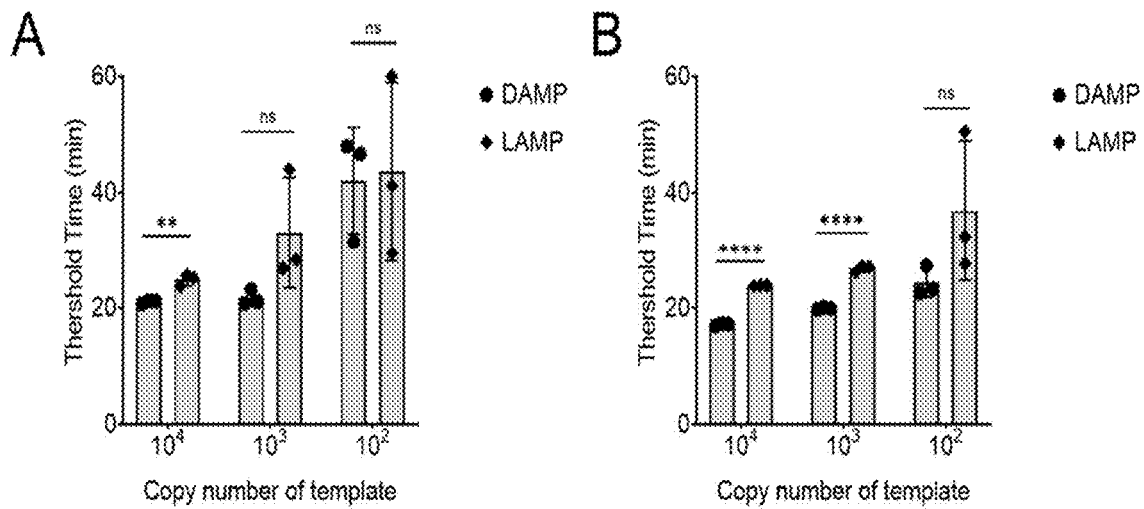
FIG. 24A-B
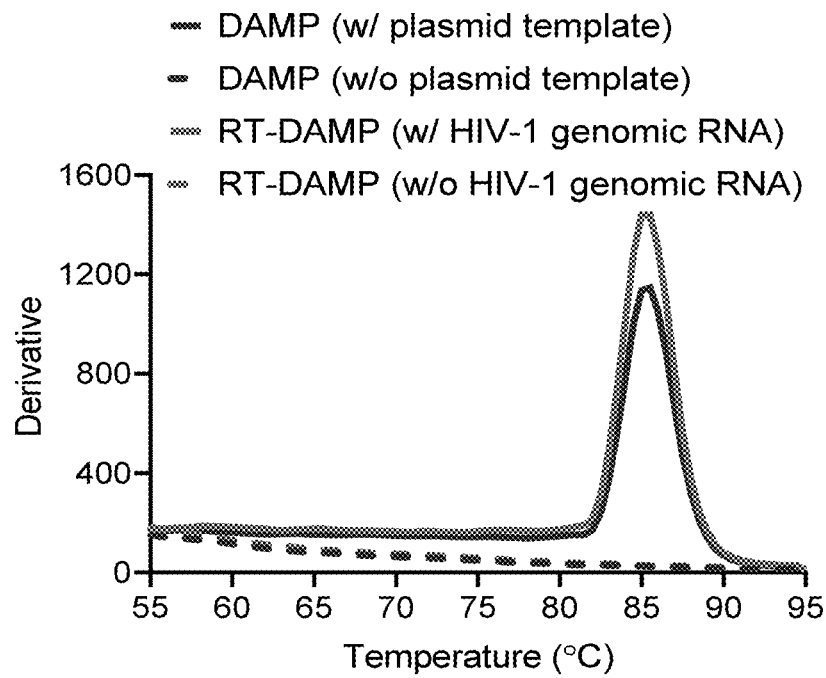
FIG. 25

SEQUENCE LISTING

```
<160> NUMBER OF SEQ ID NOS: 38

<210> SEQ ID NO 1
<211> LENGTH: 300
<212> TYPE: DNA
<213> ORGANISM: Artificial Sequence
<220> FEATURE:
<223> OTHER INFORMATION: 300-bp HIV-1 p24 gene sequence inserted into
      the pUCIDT (Amp) plasmid

<400> SEQUENCE: 1
ccagaagtaa tacccatgtt ttcagcatta tcagaaggag ccaccccaca agatttaaac      60
accatgctaa acacagtggg gggacatcaa gcagccatgc aaatgttaaa agaaaccatc     120
aatgaggaag ctgcagaatg ggatagattg catcccgtgc aggcagggcc tgttgcacca     180
ggccagataa gagatccaag gggaagtgac atagcaggaa ctaccagtac ccttcaggaa     240
caaataggat ggatgacaag taatccacct atcccagtag gagaaatcta taaaagatgg     300

<210> SEQ ID NO 2
<211> LENGTH: 19
<212> TYPE: DNA
<213> ORGANISM: Artificial Sequence
<220> FEATURE:
<223> OTHER INFORMATION: FO primer

<400> SEQUENCE: 2
attatcagaa ggagccacc                                                   19

<210> SEQ ID NO 3
<211> LENGTH: 20
<212> TYPE: DNA
<213> ORGANISM: Artificial Sequence
<220> FEATURE:
<223> OTHER INFORMATION: RO primer

<400> SEQUENCE: 3
gggataggtg gattacttgt                                                  20
```

<210> SEQ ID NO 4
<211> LENGTH: 22
<212> TYPE: DNA
<213> ORGANISM: Artificial Sequence
<220> FEATURE:
<223> OTHER INFORMATION: FC primer

<400> SEQUENCE: 4
tctgcagctt cctcattgat gg                                          22

<210> SEQ ID NO 5
<211> LENGTH: 20
<212> TYPE: DNA
<213> ORGANISM: Artificial Sequence
<220> FEATURE:
<223> OTHER INFORMATION: RC primer

<400> SEQUENCE: 5
ttgcaccagg ccagataaga                                             20

<210> SEQ ID NO 6
<211> LENGTH: 45
<212> TYPE: DNA
<213> ORGANISM: Artificial Sequence
<220> FEATURE:
<223> OTHER INFORMATION: FI primer

<400> SEQUENCE: 6
tctgcagctt cctcattgat ggttttatca agcagccatg caaat                 45

<210> SEQ ID NO 7
<211> LENGTH: 43
<212> TYPE: DNA
<213> ORGANISM: Artificial Sequence
<220> FEATURE:
<223> OTHER INFORMATION: RI primer

<400> SEQUENCE: 7
ttgcaccagg ccagataaga ttttagttcc tgctatgtca ctt                   43

<210> SEQ ID NO 8
<211> LENGTH: 45
<212> TYPE: DNA
<213> ORGANISM: Artificial Sequence
<220> FEATURE:
<223> OTHER INFORMATION: FI primer

<400> SEQUENCE: 8
tctgcagctt cctcattgat ggttttacca tgctaaacac agtgg                 45

<210> SEQ ID NO 9
<211> LENGTH: 46
<212> TYPE: DNA
<213> ORGANISM: Artificial Sequence
<220> FEATURE:
<223> OTHER INFORMATION: RI primer

<400> SEQUENCE: 9
ttgcaccagg ccagataaga ttttcctatt tgttcctgaa gggtac                46

<210> SEQ ID NO 10
<211> LENGTH: 48
<212> TYPE: DNA
<213> ORGANISM: Artificial Sequence
<220> FEATURE:

<223> OTHER INFORMATION: FI primer

<400> SEQUENCE: 10
tctgcagctt cctcattgat ggttttgcca tgcaaatgtt aaaagaaa         48

<210> SEQ ID NO 11
<211> LENGTH: 44
<212> TYPE: DNA
<213> ORGANISM: Artificial Sequence
<220> FEATURE:
<223> OTHER INFORMATION: RI primer

<400> SEQUENCE: 11
tctgcagctt cctcattgat ggttttgtca cttccccttg gatc             44

<210> SEQ ID NO 12
<211> LENGTH: 19
<212> TYPE: DNA
<213> ORGANISM: Artificial Sequence
<220> FEATURE:
<223> OTHER INFORMATION: FI primer

<400> SEQUENCE: 12
atcaagcagc catgcaaat                                         19

<210> SEQ ID NO 13
<211> LENGTH: 19
<212> TYPE: DNA
<213> ORGANISM: Artificial Sequence
<220> FEATURE:
<223> OTHER INFORMATION: RI primer

<400> SEQUENCE: 13
agttcctgct atgtcactt                                         19

<210> SEQ ID NO 14
<211> LENGTH: 19
<212> TYPE: DNA
<213> ORGANISM: Artificial Sequence
<220> FEATURE:
<223> OTHER INFORMATION: F3 primer

<400> SEQUENCE: 14
attatcagaa ggagccacc                                         19

<210> SEQ ID NO 15
<211> LENGTH: 20
<212> TYPE: DNA
<213> ORGANISM: Artificial Sequence
<220> FEATURE:
<223> OTHER INFORMATION: B3 primer

<400> SEQUENCE: 15
gggataggtg gattacttgt                                        20

<210> SEQ ID NO 16
<211> LENGTH: 45
<212> TYPE: DNA
<213> ORGANISM: Artificial Sequence
<220> FEATURE:
<223> OTHER INFORMATION: FIP primer

<400> SEQUENCE: 16
tctgcagctt cctcattgat ggttttacca tgctaaacac agtgg            45

```
<210> SEQ ID NO 17
<211> LENGTH: 46
<212> TYPE: DNA
<213> ORGANISM: Artificial Sequence
<220> FEATURE:
<223> OTHER INFORMATION: BIP primer

<400> SEQUENCE: 17
ttgcaccagg ccagataaga ttttcctatt tgttcctgaa gggtac         46

<210> SEQ ID NO 18
<211> LENGTH: 22
<212> TYPE: DNA
<213> ORGANISM: Artificial Sequence
<220> FEATURE:
<223> OTHER INFORMATION: LoopF primer

<400> SEQUENCE: 18
atttgcatgg ctgcttgatg tc                                   22

<210> SEQ ID NO 19
<211> LENGTH: 24
<212> TYPE: DNA
<213> ORGANISM: Artificial Sequence
<220> FEATURE:
<223> OTHER INFORMATION: LoopB primer

<400> SEQUENCE: 19
gaagtgacat agcaggaact acca                                 24

<210> SEQ ID NO 20
<211> LENGTH: 22
<212> TYPE: DNA
<213> ORGANISM: Artificial Sequence
<220> FEATURE:
<223> OTHER INFORMATION: Swarm primer 1

<400> SEQUENCE: 20
tctgcagctt cctcattgat gg                                   22

<210> SEQ ID NO 21
<211> LENGTH: 20
<212> TYPE: DNA
<213> ORGANISM: Artificial Sequence
<220> FEATURE:
<223> OTHER INFORMATION: Swarm primer 2

<400> SEQUENCE: 21
ttgcaccagg ccagataaga                                      20

<210> SEQ ID NO 22
<211> LENGTH: 19
<212> TYPE: DNA
<213> ORGANISM: Artificial Sequence
<220> FEATURE:
<223> OTHER INFORMATION: F primer

<400> SEQUENCE: 22
attatcagaa ggagccacc                                       19

<210> SEQ ID NO 23
<211> LENGTH: 21
<212> TYPE: DNA
<213> ORGANISM: Artificial Sequence
<220> FEATURE:
<223> OTHER INFORMATION: B primer
```

<400> SEQUENCE: 23
catcctattt gttcctgaag g                                              21

<210> SEQ ID NO 24
<211> LENGTH: 300
<212> TYPE: DNA
<213> ORGANISM: Artificial Sequence
<220> FEATURE:
<223> OTHER INFORMATION: 300-bp E. coli B malB gene sequence inserted
      into the pUCIDT (Amp) plasmid

<400> SEQUENCE: 24 gccaggggt ggaggattta agccatctcc tgatgacgca tagtcagccc atcatgaatg      60
ttgctgtcga tgacaggttg ttacaaaggg agaagggcat ggcgagcgta cagctgcaaa   120
atgtaacgaa agcctggggc gaggtcgtgg tatcgaaaga tatcaatctc gatatccatg   180
aaggtgaatt cgtggtgttt gtcggaccgt ctggctgcgg taaatcgact ttactgcgca   240
tgattgccgg gcttgagacg atcaccagcg gcgacctgtt catcggtgag aaacggatga   300

<210> SEQ ID NO 25
<211> LENGTH: 20
<212> TYPE: DNA
<213> ORGANISM: Artificial Sequence
<220> FEATURE:
<223> OTHER INFORMATION: FO primer

<400> SEQUENCE: 25
gctgtcgatg acaggttgtt                                                20

<210> SEQ ID NO 26
<211> LENGTH: 18
<212> TYPE: DNA
<213> ORGANISM: Artificial Sequence
<220> FEATURE:
<223> OTHER INFORMATION: RO primer

<400> SEQUENCE: 26
atttaccgca gccagacg                                                  18

<210> SEQ ID NO 27
<211> LENGTH: 42
<212> TYPE: DNA
<213> ORGANISM: Artificial Sequence
<220> FEATURE:
<223> OTHER INFORMATION: FI primer

<400> SEQUENCE: 27
ttttgcagct gtacgctcgt tttcaaaggg agaagggcat gg                       42

<210> SEQ ID NO 28
<211> LENGTH: 49
<212> TYPE: DNA
<213> ORGANISM: Artificial Sequence
<220> FEATURE:
<223> OTHER INFORMATION: RI primer

<400> SEQUENCE: 28
atcaatctcg atatccatga aggtgttttt ccgacaaaca ccacgaatt                49

<210> SEQ ID NO 29
<211> LENGTH: 19
<212> TYPE: DNA
<213> ORGANISM: Artificial Sequence
<220> FEATURE:

```
<223> OTHER INFORMATION: FC primer

<400> SEQUENCE: 29 tttttgcagct gtacgctcg                                               19

<210> SEQ ID NO 30
<211> LENGTH: 25
<212> TYPE: DNA
<213> ORGANISM: Artificial Sequence
<220> FEATURE:
<223> OTHER INFORMATION: RC primer

<400> SEQUENCE: 30
atcaatctcg atatccatga aggtg                                         25

<210> SEQ ID NO 31
<211> LENGTH: 18
<212> TYPE: DNA
<213> ORGANISM: Artificial Sequence
<220> FEATURE:
<223> OTHER INFORMATION: F3 primer

<400> SEQUENCE: 31
gccatctcct gatgacgc                                                 18

<210> SEQ ID NO 32
<211> LENGTH: 18
<212> TYPE: DNA
<213> ORGANISM: Artificial Sequence
<220> FEATURE:
<223> OTHER INFORMATION: B3 primer

<400> SEQUENCE: 32
atttaccgca gccagacg                                                 18

<210> SEQ ID NO 33
<211> LENGTH: 42
<212> TYPE: DNA
<213> ORGANISM: Artificial Sequence
<220> FEATURE:
<223> OTHER INFORMATION: FIP primer

<400> SEQUENCE: 33
cattttgcag ctgtacgctc gcagcccatc atgaatgttg ct                      42

<210> SEQ ID NO 34
<211> LENGTH: 40
<212> TYPE: DNA
<213> ORGANISM: Artificial Sequence
<220> FEATURE:
<223> OTHER INFORMATION: BIP primer

<400> SEQUENCE: 34
ctggggcgag gtcgtggtat tccgacaaac accacgaatt                         40

<210> SEQ ID NO 35
<211> LENGTH: 24
<212> TYPE: DNA
<213> ORGANISM: Artificial Sequence
<220> FEATURE:
<223> OTHER INFORMATION: LoopF primer

<400> SEQUENCE: 35
ctttgtaaca acctgtcatc gaca                                          24
```

```
<210> SEQ ID NO 36
<211> LENGTH: 25
<212> TYPE: DNA
<213> ORGANISM: Artificial Sequence
<220> FEATURE:
<223> OTHER INFORMATION: LoopB primer

<400> SEQUENCE: 36
atcaatctcg atatccatga aggtg                                              25

<210> SEQ ID NO 37
<211> LENGTH: 18
<212> TYPE: DNA
<213> ORGANISM: Artificial Sequence
<220> FEATURE:
<223> OTHER INFORMATION: F primer

<400> SEQUENCE: 37
gccatctcct gatgacgc                                                      18

<210> SEQ ID NO 38
<211> LENGTH: 18
<212> TYPE: DNA
<213> ORGANISM: Artificial Sequence
<220> FEATURE:
<223> OTHER INFORMATION: B primer

<400> SEQUENCE: 38
atttaccgca gccagacg                                                      18
```

ISOTHERMAL AMPLIFICATION

CROSS-REFERENCE TO RELATED APPLICATIONS

This application claims the benefit of and priority to U.S. Provisional Patent Application No. 63/076,451, filed Sep. 10, 2020, the content of which is hereby incorporated by reference in its entirety.

STATEMENT OF GOVERNMENT SUPPORT

This invention was made with government support under award numbers R01CA214072, R21TW010625, and R01EB023607 awarded by the National Institutes of Health. The government has certain rights in the invention.

SEQUENCE LISTING

The Instant Application contains a Sequence Listing which has been submitted electronically in ASCII format and is hereby incorporated by reference in its entirety. Said ASCII copy, created on Jun. 2, 2023 is named "UCT0275US2_ST25" and is 8,001 bytes in size. The Sequence Listing does not go beyond the disclosure in the application as filed.

BACKGROUND

Generation of multiple copies of a particular nucleic acid is often necessary or helpful for the nucleic acid to be used for a given application. For example, to analyze the nucleotide sequence of a nucleic acid of interest, frequently, the nucleic acid is replicated to increase its copy number before the sequence is analyzed. In another example, to determine the presence or absence of a particular nucleic acid in a sample, a sample may be treated under conditions such that if the particular nucleic acid is present in the sample, it may be amplified. In another example, a nucleic acid for use as probe may be copied repeatedly to generate many nucleic acids containing the same sequence as the original nucleic acid template, thereby generating many copies of the nucleic acid which may be used as a probe.

A variety of methods for the amplification of nucleic acids are known. For example, the polymerase chain reaction ("PCR") (see, e.g., U.S. Pat. No. 4,683,202) is a popular method for the amplification of nucleic acids. To successfully perform a PCR reaction, the reaction must be performed at multiple different temperatures. This requires hardware or other mechanisms for repeatedly changing the temperature of the PCR reaction. Another method for amplification of nucleic acids is referred to as loop-mediated isothermal amplification ("LAMP") (see, e.g., U.S. Pat. No. 6,410,278). LAMP reactions may be performed isothermally, but typically involve the use of four different primers which recognize a total of six distinct sequences on the target nucleic acid.

To facilitate the generation of amplified nucleic acids for the many and growing number of applications which use amplified nucleic acids, new methods, and reagents for the amplification of nucleic acids are desired.

SUMMARY

Disclosed herein are "dual-priming" isothermal amplification methods (including "self-priming" and "pairing-priming" strand extension, termed "DAMP") for rapid nucleic acid detection. In some embodiments, the disclosed methods also are simple, versatile, sensitive, and/or specific methods for nucleic acid detection.

In an aspect, disclosed herein are methods of amplifying a target DNA, comprising
  contacting a DNA sample suspected of containing the target DNA with primers, and
  amplifying the target DNA,
  wherein the primers comprise
    a forward outer primer (FO),
    a reverse outer primer (RO),
    a forward inner primer (FI),
    a reverse inner primer (RI),
    a forward reverse pairing-competition primer (FC), and
    a reverse pairing-competition primer (RC).

In some embodiments, the target DNA comprises 5' to 3', an F3 site, an F2 site, and F1 site, an R1 site, and R2 site and an R3 site.

In some embodiments, the complement to the target DNA comprises 3' to 5', an F3c site, an F2c site, and F1c site, an R1c site, and R2c site and an R3c site.

In some embodiments, the forward outer primer (FO) is complementary to the F3c site.

In some embodiments, the reverse outer primer (RO) complementary to the R3 site.

In some embodiments, the forward inner primer (FI) comprises the F1c and F2 sites separated by a TTTT spacer.

In some embodiments, the FI provides about 10 nucleotides to about 40 nucleotides from the first nucleotide of the F2 site to the first nucleotide of the F1 site in the target sequences.

In some embodiments, the FI provides about 22 nucleotides from the first nucleotide of the F2 site to the first nucleotide of the F1 site in the target sequences.

In some embodiments, the FI provides about 30 nucleotides from the first nucleotide of the F2 site to the first nucleotide of the F1 site in the target sequences.

In some embodiments, the reverse inner primer (RI) comprises the R1 and R2c sites separated by a TTTT spacer.

In some embodiments, the RI provides a distance of about 10 nucleotides to about 40 nucleotides from the first nucleotide of R2c to the first nucleotide of R1c.

In some embodiments, the RI provides a distance of about 22 nucleotides from the first nucleotide of R2c to the first nucleotide of R1c.

In some embodiments, the RI provides a distance of about 30 nucleotides from the first nucleotide of R2c to the first nucleotide of R1c.

In some embodiments, the forward reverse pairing-competition primer (FC) is complementary to the R1 site.

In some embodiments, the reverse pairing-competition primer (RC) complementary to the F1c site.

In some embodiments, FO, RO, FC and RC are single site primers.

In some embodiments, FI and RI are double site primers.

In some embodiments, the primers that contact the sample DNA specifically recognize distinct sites flanking the F3, F2, and R1 sites of the forward target sequence and the R3c, R2c, F1c sites of the target reverse sequence, respectively.

In some embodiments, amplifying the target DNA comprises
  producing a basic structure; and
  cyclically amplifying the basic structure to provide amplified target DNA.

In some embodiments, producing the basic structure comprises contacting the sample with the FO, FI, RI, and RO primers.

In some embodiments, the sample is contacted with the FO, FI, RI, and RO primers under conditions for DNA synthesis.

In some embodiments, the basic structure comprises from 5' to 3', R1, R2c, R1c, F1c, F2c, and F1.

In some embodiments, the basic structure is cyclically amplified by contacting the basic structure with F1, R1, FC and Rc.

In another aspect, provided herein are methods of amplifying a target DNA, comprising contacting a DNA sample suspected of containing the target DNA with six primers, and amplifying the target DNA, wherein the target DNA comprises 5' to 3', an F3 site, an F2 site, and F1 site, an R1 site, and R2 site and an R3 site, and the complement to the target DNA comprises, 3' to 5', an F3c site, an F2c site, and F1c site, an R1c site, and R2c site and an R3c site, wherein the six primers comprise a forward outer primer (FO) complementary to the F3c site, a reverse outer primer (RO) complementary to the R3 site, a forward inner primer (FI) comprising the F1C and F2 sites separated by a TTTT spacer, wherein FI provides a distance of less than 40 nucleotides from the first nucleotide of the F2 site to the first nucleotide of the F1 site in the target sequences, a reverse inner primer (RI) comprising the R1 and R2c sites separated by a TTTT spacer, wherein RI provides a distance of less than 40 nucleotides from the first nucleotide of R2c to the first nucleotide of R1c, a forward reverse pairing-competition primer (FC) complementary to the F1 site, and a reverse pairing-competition primer (RC) complementary to the R1c site, wherein FO, RO, FC and RC are single site primers, and FI and RI are double site primers, wherein the six primers specifically recognize distinct sites flanking the F3, F2, and R1 sites of the forward target sequence and the R3c, R2c, F1c sites of the target reverse sequence, respectively, wherein amplifying the target DNA comprises producing a basic structure by contacting the sample with the FO, FI, RI, and RO primers under conditions for DNA synthesis, wherein the basic structure comprises, from 5' to 3', R1, R2c, R1c, F1c, F2c, F1, and cyclically amplifying the basic structure by contacting the basic structure with F1, RC, FC and R1c to provide amplified target DNA.

BRIEF DESCRIPTION OF THE FIGURES

FIGS. 1A-1C illustrate the principle of the dual-priming isothermal amplification (DAMP) reaction. FIG. 1A shows the primer design for DAMP. FIG. 1B shows the basic producing step. FIG. 1C shows the cycling amplification step.

FIGS. 2A-2C show the length and melting temperature ($T_m$) for each target site used for the DAMP primer design when the target sequence is AT-rich (FIG. 2A), normal (FIG. 2B), and GC-rich (FIG. 2C).

FIGS. 3A-3C show the continued cycling amplification step for the DAMP process, including Pathway 1 (FIG. 3A), Pathway 2 (FIG. 3B), and complementary Pathway 2* (FIG. 3C).

FIG. 3D shows the main dsDNA products for DAMP reactions.

FIGS. 4A-4C show optimization of the DAMP primers concentrations: FO and RO (FIG. 4A), FI and RI (FIG. 4B), and FC and RC (FIG. 4C). $10^5$ copies HIV-1 cDNA templates were used as template in the DAMP assay. Error bars represent the standard deviations at three replicates (n=3).

FIG. 4D shows a real-time fluorescence DAMP assay of HIV DNA using the optimal primer concentration. Positive, three replicated reactions with $10^5$ copies HIV-1 p24 gene cDNA templates. NTC, three replicated non-template control reactions.

FIGS. 5A-5D show a comparison of the six-primer LAMP and DAMP assay for the detection of HIV-1 DNA by targeting the same DNA sequence. FIG. 5A shows the primer design of six-primer LAMP (Left) and its real-time fluorescence LAMP detection (Right). FIG. 5B shows the primer design of DAMP (Left) and its real-time fluorescence DAMP detection (Right). FIG. 5C shows electropherograms of DAMP and six-primer LAMP products in a 3% agarose gel. FIG. 5D shows a comparison of endpoint fluorescence intensity of the DAMP products and six-primer LAMP products after 60-min reactions. Error bars represent the standard deviations at six replicates (n=6). Positive, 105 copies HIV-1 p24 gene cDNA templates. NTC. three replicated non-template control reactions.

FIGS. 6A-6F show a comparison of the DAMP (RT-DAMP) and six-primer LAMP (RT-LAMP) assays for HIV-1 DNA (RNA) detection and versatility evaluation of our DAMP assay by detecting E. coli DNA. FIG. 6A shows the sensitivity of DAMP assay for the detection of HIV-1 p24 gene cDNA sequence. FIG. 6B shows the threshold time and its linear relationship with the $\log_{10}$ of copy number of HIV DNA templates for DAMP and six-primer LAMP. FIG. 6C shows the sensitivity of RT-DAMP for the detection of HIV-1 genomic RNA extracted from HIV-1 plasma control samples. FIG. 6D shows the sensitivity of RT-LAMP for the detection of HIV-1 genomic RNA extracted from HIV-1 plasma control samples. FIG. 6E shows the sensitivity of DAMP to amplify the E. coli B malB gene sequence. FIG. 6F shows the linear relationship between threshold time and the $\log_{10}$ of copy number of E. coli DNA templates by using our DAMP assay and the previously reported six-primer LAMP. Cps, copy number. Three replicates were set up for every reaction. NTC, three replicated non-template control reactions. Error bars represent the standard deviations of threshold times at three replicates (n=3).

FIGS. 7A-7B show the principle of the loop-mediated isothermal amplification (LAMP) with two loop primers (six-primer LAMP) method. FIG. 7A shows the primer design of the six-primer LAMP reaction. FIG. 7B shows the dumbbell structure producing step of a six-primer LAMP.

FIGS. 8A-8C show the length and melting temperature ($T_m$) for each target site used for DAMP primer design when the target sequence is AT-rich (FIG. 8A), normal (FIG. 8B), and GC-rich (FIG. 8C).

FIG. 9A-9C show continued cycling amplification step for DAMP reaction includes: Pathway 1 (FIG. 9A), Pathway 2 (FIG. 9B), and complementary Pathway 2* (FIG. 9C).

FIG. 9D shows the main dsDNA products in the DAMP reactions.

FIGS. 10A-10C show agarose gel electrophoresis analysis and the melting curve analysis of the products of DAMP assays with 55/56 nt (FIG. 10A), 30 nt (FIG. 10B), and 22 nt (FIG. 10C) distance of the two target sites for each inner primer design to detect various copies of targets (from $4 \times 10^8$ to $4 \times 10^2$ copies). M, 50 bp DNA ladder marker. NTC, non-template control.

FIGS. 11A-11C evaluate the influence of various primer designs on DAMP efficiency. FIG. 11A shows primer design with single-site inner primers (Left) and its real-time fluorescence isothermal amplification curves (Right). FIG. 11B shows primers design without including FC and RC primers (Left) and the real-time fluorescence isothermal amplification curves (Right). FIG. 11C shows primer design of typical DAMP (Left) and its real-time fluorescence DAMP curves (Right). The 300-bp HIV-1 p24 gene cDNA sequence was used as the target sequence which was inserted into a plasmid. The vertical gray dash line denotes the same amplification region. Positive, three replicated reactions with $10^5$ copies templates. NTC, three replicated non-template control reactions.

FIGS. 19A-19B show real-time fluorescence curves (FIG. 19A) and melting curve analysis (FIG. 19B) of the DAMP and LAMP products of non-template control (NTC). Three replicates were run for each reaction or test.

FIG. 20 shows a threshold time comparison of $10^5$ copies of PV DNA templates detected by the DAMP and the six-primer LAMP. The 300-bp HIV-1 p24 gene cDNA sequence was the target sequence. The positive was the reaction with $10^5$ copies templates. Error bars represent the standard deviations at three replicates (n=3).

FIGS. 21A-21D shows a comparison of DAMP with different LAMP variants. FIG. 21A shows four-primer LAMP primer design (Left) and its real-time fluorescence signals (Right). FIG. 21B shows four-primer LAMP with swarm primers (Left) and its real-time fluorescence signals (Right). FIG. 21C shows six-primer LAMP with swarm primers (Left) and its real-time fluorescence signals (Right). FIG. 21D shows DAMP (Left) and its real-time fluorescence signals (Right). 300-bp HIV-1 p24 gene cDNA sequence inserted into a plasmid was the target sequence. The vertical gray dash line denotes the same amplification region. Positive, three replicated reactions with $10^5$ copies templates. NTC, three replicated non-template control reactions.

FIGS. 22A-22B shows real-time fluorescence signals of DAMP (FIG. 22A) and six-primer LAMP (FIG. 22B) to amplify the same target sequence (HIV DNA) in two-hour incubation. 300-bp HIV-1 p24 gene cDNA sequence inserted into a plasmid was the target sequence. Positive, three replicated reactions with $10^5$ copies templates. NTC, three replicated non-template control reactions.

FIGS. 23A-23D show a comparison of the sensitivities of the DAMP assay and PCR assay for detection of different gene sequences. FIG. 23A shows the sensitivity of DAMP assay for the detection of HIV-1 p24 gene cDNA sequence. FIG. 23B shows the sensitivity of the PCR assay for the detection of HIV-1 p24 gene cDNA sequence. FIG. 23C shows the sensitivity of the DAMP assay for the detection of E. coli B malB gene sequences. (FIG. 23C shows the sensitivity of the PCR assay for the detection of E. coli B malB gene sequences. Error bars represent the standard deviations at three replicates (n=3). Cps, copy number. Three replicates were set to amplify each cps of targets. NTC, three replicated non-template control reactions.

FIGS. 24A-24B shows a comparison of threshold time for DAMP and LAMP using the templates with copies number at $10^4$, $10^3$, and $10^2$. FIG. 24A is for the detection of p24 gene sequence. FIG. 24B is for the detection of malB gene sequence. Three replicates ran for each reaction or test. Error bars represent the standard deviations at three replicates (n=3). Unpaired two-tailed t test was used to analyse the difference. *$P<0.05$; $P<0.01$; *$P<0.001$; ****$P<0.0001$. ns, not significant.

FIG. 25 shows the melting curves of the DAMP product of plasmids containing HIV-1 p24 gene (100 copies) and the RT-DAMP product of HIV-1 genomic RNA (350 copies) extracted from HIV virus in human plasma.

DETAILED DESCRIPTION

Figure 12:
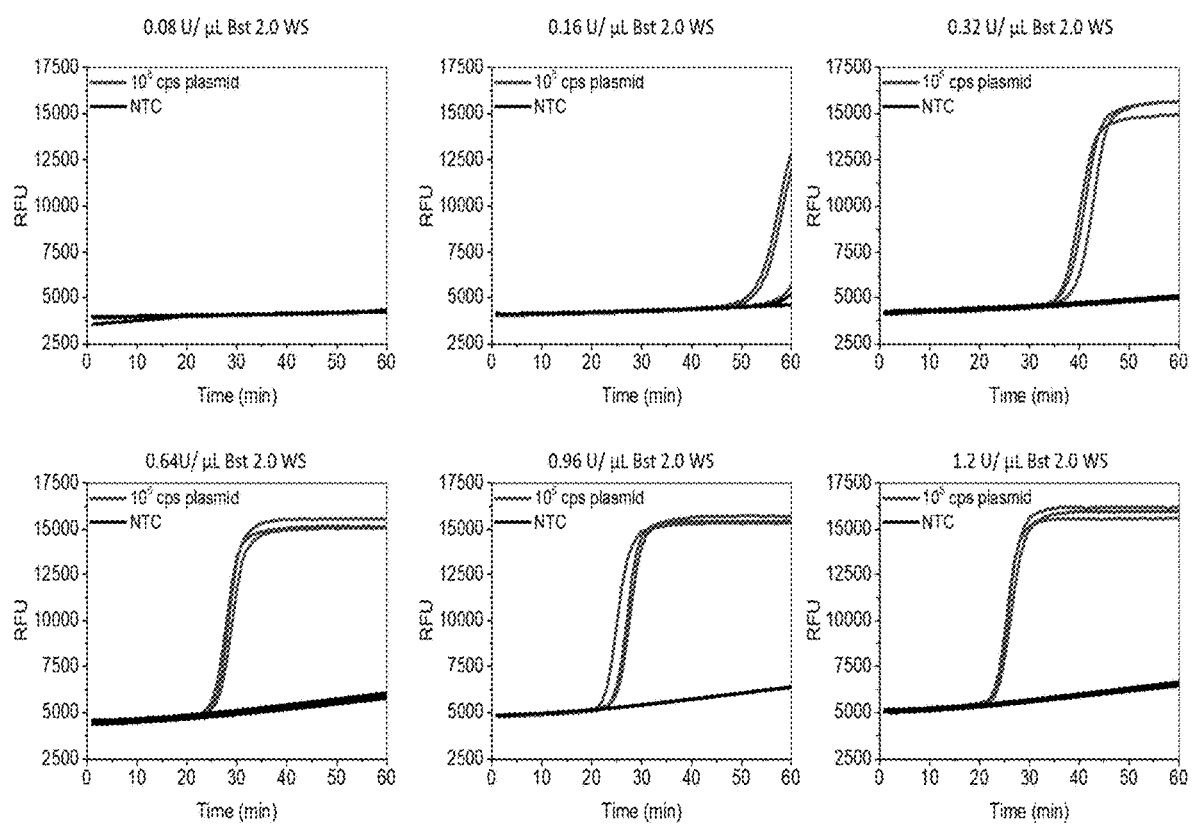
FIG. 12 shows real-time fluorescence signals of DAMP assay using various amounts of Bst 2.0 WarmStart® DNA polymerase (Bst 2.0 WS). The 300-bp HIV-1 p24 gene cDNA sequence inserted into a plasmid was the target sequence. Positive, three replicated reactions with $10^5$ copies templates. NTC, three replicated non-template control reactions.

Nucleic acid amplification tests (NAATs) have been used in many fields including clinical molecular diagnostics, food safety monitoring, gene expression analysis, and fundamental molecular biology (Schachter et al. Sex. Transm. Dis. 2008, 35, 637-42; Rodriguez-Lazaro et al. Trends Food Sci. Technol. 2007, 18, 306-19; Pai et al. The Lancet infectious diseases 2003, 3, 633-43; Monis, P. T.; Giglio Infect. Genet. Evol. 2006, 6, 2-12). The polymerase chain reaction (PCR) is the most common approach for DNA amplification and pathogen identification in clinical microbiology laboratories. However, PCR typically requires expensive equipment and well-trained personnel, which is not suitable for point of care diagnostics, and/or testing in resource-limited settings. For the past few decades, with the rapid development of enzyme engineering and molecular biology, NAATs have been significantly simplified with emerging isothermal amplification technologies (Zhao et al. *Chem. Rev.* 2015, 115, 12491-545), such as loop-mediated isothermal amplification (LAMP; Notomi et al. *Nucleic Acids Res.* 2000, 28, e63-e636), nucleic acid sequence based amplification (NASBA; Gabrielle et al. *Microbiology* 1993, 139, 2423-29), recombinase polymerase amplification (RPA; Piepenburg et al. *PLoS Biol.* 2006, 4, e204), and helicase dependent amplification (HAD; Vincent et al. *EMBO Rep.* 2004, 5, 795-800). Among these, the LAMP method is one of the most widely used isothermal amplification assays for pathogen detection due to its simplicity, rapidity, high sensitivity, and cost-effectiveness.

The earliest LAMP technology proposed by Notomi et al. used four primers to recognize six distinct regions of target DNA, termed "four-primer LAMP." However, the four-primer LAMP assay is too slow for many clinical diagnostic applications. To improve amplification efficiency and shorten detection time, several LAMP variants have been developed by adding loop primers (Nagamine et al. *Mol. Cell. Probes* 2002, 16, 223-29), stem primers (Gandelman et al. *Int. J. Mol. Sci.* 2011, 12, 9108-24), and swarm primers (Martineau et al. *Anal. Chem.* 2016, 89, 625-32). Of these variants, LAMP with two loop primers (termed "six-primer LAMP") has prevailed following the addition of loop primers which greatly improved amplification efficiency and reduced testing time. Although stem primers were developed to accelerate the amplification reaction, they added a challenge to the primer design of the six-primer LAMP since six primers need to recognize eight distinct sites of the target DNA. To reduce the number of target sites, swarm primers were proposed to be added to the LAMP. Unfortunately, the amplification efficiency of the LAMP with swarm primers only is lower than that of the LAMP with loop or stem primers. To ensure rapid amplification, loop/stem primers were added to the LAMP with swarm primers, which increases the total number of target sites up to ten. However, the nature of increasing target sites in the LAMP assays is prone to form primer dimers and leads to undesired non-specific amplification, which limits the detection reliability and specificity in clinical diagnostic applications. Furthermore, all these LAMP methods mainly rely on the inner primers to initiate a "self-priming" strand extension during the isothermal amplification with less ability to simultaneously generate multiple basic structures for cycling amplification.

Disclosed herein is a "dual-priming" isothermal amplification method (including "self-priming" and "pairing-priming" strand extension, termed "DAMP") for highly sensitive and specific nucleic acid detection with ultralow nonspecific signals. To enable a fairly competitive strand extension between "self-priming" and "pairing-priming", two strategies were incorporated into the disclosed DAMP assay: i) the inner primer design was modified by reducing the distance of its two target sites below 40 nucleotides (nt) (typically 40-60 nt for conventional LAMP method15), and ii) two pairing-competition primers were added to recognize the sites at the free 3'-end parts of the basic structures. The pairing-competition primers compete with the "self-priming" extension to enable efficient "pairing-priming" extension, thereby generating multiple basic structures simultaneously (e.g., the initial amplicons generated by the inner primers) for cycling amplification.

Studies demonstrated that "dual-priming" strand extension is critical to achieve a highly sensitive and reliable DAMP assay. The performance of the disclosed DAMP assay was evaluated by detecting HIV-1 DNA/RNA and *Escherichia coli* (*E. coli*) DNA, which showed that DAMP assay had equal or better sensitivity with faster amplification speed compared to conventional LAMP and PCR assays. In some embodiments, the disclosed DAMP assay gave ultralow, nonspecific background signals even after two-hour incubation.

Definitions

Throughout the present specification and the accompanying claims, the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. No language in the specification should be construed as indicating any non-claimed element essential to the practice of the invention.

The terms "a," "an," and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximately") one particular value, and/or to "about" (or "approximately") another particular value. When such a range is expressed, another embodiment includes from the one particular value and/or to the other particular value. Similarly, when values are expressed as approximations, by use of the antecedent "about" or "approximately" it will be understood that the particular value forms another embodiment. It will be further understood that the endpoints of each of the ranges are disclosed both in relation to the other endpoint, and independently of the other endpoint.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g., "such as") provided herein is intended merely to better illuminate the invention and does not pose a limitation on the scope of the invention otherwise claimed.

Units, prefixes, and symbols are denoted in their Systeme International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

As used herein, the term "about" refers to a range of values of plus or minus 10% of a specified value. For example, the phrase "about 200" includes plus or minus 10% of 200, or from 180 to 220, unless clearly contradicted by context.

As used herein, "optional" or "optionally" means that the subsequently described event or circumstance may or may not occur, and that the description includes instances where said event or circumstance occurs and instances where it does not.

Dual-Priming Mediated Isothermal Amplification (Damp)

Described herein is a new isothermal nucleic acid amplification method, termed dual-priming mediated isothermal amplification (DAMP), for molecular detection with high sensitivity and specificity. One of the big challenges of current loop-mediated isothermal amplification (LAMP), especially the LAMP with two loop primers, is to easily generate false positive result due to the forming of primer-dimers. To this end, a new DAMP assay was developed to enable highly efficient amplification of nucleic acid with ultralow nonspecific amplification.

DAMP can be used to develop a variety of molecular diagnostic kits for the applications including, but not limited to, pathogen detection, the identification of genetically modified organisms, the analysis of clinical biomarkers, and point-of-care diagnostic testing. The end users can be medical personnel, the personnel at Centers for Disease Control (CDC), the inspector of food safety and animal health from agricultural sector, and the quarantine officers from customs administration.

Briefly, the principle of the DAMP is illustrated in FIG. 1. A total of six sequence-specific primers are designed in DAMP, including the forward and reverse outer primers of FO and RO, the forward and reverse inner primers of FI and RI, and the forward and reverse pairing-competition primers of FC and RC. These six primers specifically recognize six distinct sites flanking the F3, F2, R1 sites of the forward target sequence and the R3c. R2c, F1c sites of the target reverse sequence (see FIG. 1A). F and R mean the "forward and reverse" directions, respectively. The lowercase "c" represents "complementary". For example, the F3c and F3 sites are complementary sequences.

As shown in FIG. 1A, both the outer- and pairing-competition primers are single-site primers. FO (RO) primer uses the F3 (R3c) site and FC (RC) primer employs the R1 (F1c) site. In contrast, the inner primers are double-site primers. FI primer is composed of F1c and F2 sites with a "TTTT" four-thymine spacer, and the F2 site is at the 3'-end. RI primer consists of R1, the "TTTT" spacer, and R2c. The TTTT spacer is introduced into the inner primers to destabilize the primer-dimers. Compared to conventional LAMP primers design, the DAMP method has two distinct features: i) each inner primer is designed to recognize two target sites with the distance below 40 nt and inserted with a TTTT spacer, which ensures efficient "dual-priming" extension. However, in the LAMP method, the distance between two target sites of the inner primers is recommended to be 40-60 nt to initiate efficient "self-priming" extension according to the LAMP primer design guide. Second, to accelerate the amplification, two pairing competition primers are added. But the addition of the pairing-competition primers does not increase the total number of target sites and complicates the primer design because their sequences are the same as the 5'-parts of the inner primers (FI/RI). The length and melting temperature ($T_m$) for each site are summarized in FIG. 2.

The DAMP assay typically contains two steps: i) basic structure producing step (FIG. 1B) and ii) cycling amplification step (FIG. 1C and FIG. 3). To facilitate explanation of the DAMP amplification mechanism, a reverse target sequence was used as an example. In the DAMP assay, DNA synthesis is initiated by DNA polymerase when the F2 region of FI primer anneals to the F2c site and the FO primer anneals to the F3c site. Due to the strand-displacement activity of the DNA polymerase, the strand elongated from FI primer is displaced and released by the FO primer extension. Then, R2 and R3 sites in the released strand are recognized by RI and RO primers, respectively.

Afterwards, the extended strand by RI primer is displaced by the elongated strand from RO primer. The released strands form basic structure (termed "Basic Structure 1" in FIG. 1B) for the downstream cycling amplification. Since the RI primer contains two target sites with a distance of less than 40 nt and a TTTT spacer, the "self-priming" strand extension capability in Basic Structure 1 is reduced compared to the dumb-bell structure in conventional LAMP method. Furthermore, due to the addition of pairing competition primers, the weakened "self-priming" extension (Item 1 in the black box in FIG. 1C) will fully compete with three "pairing-priming" extension events: i) the first "pairing-priming" extension is initiated by the annealing of F2 site in FI primer to the F2c site (Item 2 in the box), ii) the second one results from the annealing competition of FC primer to the FI site (Item 3 in the box), and iii) the third one is the concurrence of the aforementioned two events (Item 4 in the box). The "self-priming" extension is able to produce dsDNA fragments with a closed loop which can be recognized by FI primer.

Then, the "self-priming" and "pairing-priming" strand extensions take place at their 3'-end parts again, and the amplification proceeds to Pathway 1. Unlike "self-priming" extension, the "pairing-priming" extension can simultaneously generate multiple basic structures for cycling amplification, including duplex basic structure and the complementary basic structure (Basic Structure 2 in FIG. 1C). However, only one dumb-bell structure is produced at this step in the conventional LAMP, due to strong "self-priming" but weak "pair-priming" strand extension. Analogously, "self-priming" and "pairing-priming" extensions occur at both ends of the duplex basic structure, then stepping into Pathways 1 and 2. Whereas, Basic Structure 2 only has "self-priming" and "pairing-priming" both occurring at its 3'-end part, subsequently moving into Pathway 2. In Pathways 1 and 2, owing to the co-mediation effect of "self-priming" and "pairing priming" extensions, Basic Structure 1 and 2 are generated again to recycle the amplification. In addition, growing dsDNA structures are produced to constitute the main products. Details on these two pathways are shown in FIG. 3.

Advantages of Damp

DAMP achieves ultralow nonspecific amplification to potentially reduce the occurrence of false positive results, which improves the detection accuracy and reliability.

DAMP is faster on amplification speed and has the comparable sensitivity to the conventional methods including LAMP and PCR.

DAMP is a universal method for the detection of various nucleic acid targets.

Loop-mediated isothermal amplification (LAMP) is a conventional amplification method. However, the current LAMP assay, especially the LAMP with two loop primers, has high nonspecific amplification due to forming of primer-dimers, which limits the use of the LAMP method for accurate and reliable clinical applications.

Compared to the conventional LAMP, the DAMP method has two distinct features on primers design. First, each inner primer in DAMP is designed to recognize two target sites with the distance below 40 nucleotides (nt) and inserted with a TTTT spacer, which ensures efficient "dual-priming" extension. However, in the LAMP method, the distance between the two target sites used for inner primer design is recommended to be 40-60 nt to initiate efficient "self-priming" extension according to the LAMP primer design guide. Second, to accelerate the amplification, two pairing competition primers are added. But the addition of the pairing-competition primers does not increase the total number of target sites and complicates the primer design because their sequences are the same as the 5'-parts of the inner primers.

Due to the unique inner primer design and the addition of two pairing competition primers, DAMP has showed an ultralow nonspecific signal even after two-hour incubation. In addition, the DAMP assay has higher amplification efficiency owing to its "dual-priming" strand extension which benefits generating multiple basic structures simultaneously for cycling amplification. Furthermore, DAMP has simpler primer design and the reduced potential risk of false-positive, since the used six primers only recognize six target sites.

All references and publications included herein are incorporated by reference. The following examples are not intended to be limiting.

EXEMPLIFICATION

Example: Dual-Priming Isothermal Amplification (Damp) for Highly Sensitive and Specific Molecular Detection with Ultralow Nonspecific Signals In this example, a DAMP (RT-DAMP) method was developed for highly sensitive and specific nucleic acid isothermal amplification. This method takes advantage of a "dual-priming" extension mechanism to enable highly reliable and specific molecular detection.

Materials and Reagents

Fluorescent dye EvaGreen® (20× in water) was purchased from Biotium (Fremont, CA). Agarose powder, 50×TAE (Tris/Acetic Acid/EDTA) Buffer, and SsoAdvanced™ Universal SYBR® Green PCR Supermix were purchased from Bio-Rad Laboratories (Hercules, CA). Deoxynucleotide (dNTP) solution mix (10 mM of each), $Mg_2SO_4$ (100 mM), *Bacillus stearothermophilus* (Bst) 2.0 WarmStart® DNA polymerase (8000 U/mL), WarmStart® RTx Reverse Transcriptase (15,000 units/mL), extreme thermostable single-stranded DNA binding protein (ET SSB, 500 µg/mL), 10× Isothermal Amplification Buffer (200 mM Tris-HCl, 500 mM KCl, 100 mM $(NH_4)_2SO_4$, 20 mM $MgSO_4$, 1.0% Tween® 20 and pH 8.8 at 25° C.), and 10 ThermoPol® Reaction Buffer (200 mM Tris-HCl, 100 mM KCl, 100 mM $(NH_4)_2SO_4$, 20 mM $MgSO_4$ and 1% Triton X-100, pH 8.8 at 25° C.) were all purchased from New England BioLabs (Ipswich, MA). RNeasy® Mini Kit for RNA extraction was purchased from QIAGEN (Frederick, MD). AcroMetrix™ HIV-1 Controls was purchased from Thermo Fisher Scientific (Waltham, MA). Oligonucleotides (primers) and the pUCIDT (Amp) plasmid containing 300-bp HIV-1 p24 gene or 300-bp *E. coli* B malB gene sequence were ordered from Integrated DNA Technologies (Coralville, IA).

Damp and RT-Damp Assays

For the DAMP assay, a total of six primers were used to recognize six different target sites (FIG. 1A), including the forward and reverse outer primers (FO and RO primers), the forward and reverse inner primers (FI and RI primers), as well as forward and reverse pairing-competition primers (FC and RC primers). The DAMP primers were manually designed using the OligoAnalyzer Tool and the PrimerExplorer (primerexplorer.jp/e/) according to the principle of primer design. Alternatively, an online primer design platform also was developed to assist DAMP primer design. The optimal DAMP reaction system contained 0.2 µM each of FO and RO primers, 1.6 µM each of FI and RI primers, 1.6 µM each of FC and RC primers, 1× EvaGreen®, 0.2 M betaine, 1× Isothermal Amplification Buffer (20 mM Tris-HCl, 50 mM KCl, 10 mM $(NH_4)_2SO_4$, 2 mM $MgSO_4$, and 0.1% Tween® 20), 1.2 U/µL Bst 2.0 WarmStart® DNA polymerase, 1.6 mM of each dNTP, 4 mM $MgSO_4$, and 1.0 µL of plasmid template solution. Before adding the DNA templates for isothermal amplification, the plasmid template solutions were denatured first by heating to 95° C. for 5 min and then chilling on ice for 5 min. The optimal RT-DAMP reaction system was the same as the optimal DAMP reaction system, except for the addition of 0.3 U/µL WarmStart® RTx Reverse Transcriptase and 2.5 ng/µL Extreme Thermostable Single-stranded DNA Binding Protein (ET SSB). The sequences of primers and targets are shown in Table 1.

Lamp and RT-Lamp Assays

The LAMP primers were all designed using the online PrimerExplorer. The optimal LAMP reaction protocol was developed according to the guideline of New England BioLabs, which substantially consisted of 0.2 µM each of F3 and B3 primers, 1.6 µM each of FIP and BIP primers, 0.4 µM each of LoopF and LoopB primers, 1× EvaGreen®, 1× Isothermal Amplification Buffer, 0.32 U/µL Bst 2.0 WarmStart® DNA polymerase, 1.4 mM of each dNTP, 6 mM $MgSO_4$, and 1.0 µL of plasmid template solution. The RT-LAMP reaction system was similar to the LAMP reaction system but was supplemented with 0.3 U/µL WarmStart® RTx Reverse Transcriptase and 2.5 ng/µL ET SSB. The reaction systems for LAMP with swarm primers were the same as what was reported previously by Martineau et al. (*Anal. Chem.* 2016, 89, 625-32). For the LAMP assay of *E. coli* B malB gene sequence, the primer sequences and LAMP assay protocol were similar to Hill et al. (*J. Clin. Microbiol.* 2008, 46, 2800-04).

PCR Assay

SsoAdvanced™ Universal SYBR® Green Supermix from the Bio-Rad Laboratories was used for the PCR assay. According to the instruction manual, the PCR reaction system contained 1× Supermix, 400 nM each of primers, and 1.0 µL of plasmid template solution. The thermal cycling protocol included 2.5 min at 98° C. for initial denaturation, 35 cycles of 15 s at 95° C. for denaturation and 30 s at 60° C. for annealing and extension, and the melt-curve analysis (from 65° C. to 95° C. with 0.5° C. increment). The sequences of primers and targets are shown in Table 1.

TABLE 1

LIST OF SEQUENCE INFORMATION OF THE PRIMERS AND TARGETS

| Item | Sequence (5'-3') | Description | SEQ ID NO: |
|---|---|---|---|
| For the amplification of HIV-1 p24 gene sequence | | | |
| The 300-bp HIV-1 p24 gene sequence inserted into the pUCIDT (Amp) plasmid | CCAGAAGTAATACCCATGTTTTCAGCATTAT CAGAAGGAGCCACCCCACAAGATTTAAACAC CATGCTAAACACAGTGGGGGGACATCAAGC AGCCATGCAAATGTTAAAAGAAACCATCAAT GAGGAAGCTGCAGAATGGGATAGATTGCATC CCGTGCAGGCAGGGCCTGTTGCACCAGGCCA GATAAGAGATCCAAGGGGAAGTGACATAGC AGGAACTACCAGTACCCTTCAGGAACAAATA GGATGGATGACAAGTAATCCACCTATCCCAG TAGGAGAAATCTATAAAAGATGG | | 1 |
| FO primer | ATTATCAGAAGGAGCCACC | | 2 |
| RO primer | GGGATAGGTGGATTACTTGT | | 3 |
| FC primer | TCTGCAGCTTCCTCATTGATGG | | 4 |
| RC primer | TTGCACCAGGCCAGATAAGA | | 5 |
| FI primer | TCTGCAGCTTCCTCATTGATGGTTTTATCAAG CAGCCATGCAAAT | Inner primers using target sites with 30 nt distance | 6 |
| RI primer | TTGCACCAGGCCAGATAAGATTTTAGTTCCT GCTATGTCACTT | Inner primers using target sites with 30 nt distance | 7 |
| FI primer | TCTGCAGCTTCCTCATTGATGGTTTTACCATG CTAAACACAGTGG | Inner primers using target sites with 55 nt distance | 8 |
| RI primer | TTGCACCAGGCCAGATAAGATTTTCCTATTT GTTCCTGAAGGGTAC | Inner primers using target sites with 56 nt distance | 9 |
| FI primer | TCTGCAGCTTCCTCATTGATGGTTTTGCCATG CAAATGTTAAAAGAAA | Inner primers using target sites with 22 nt distance | 10 |
| RI primer | TCTGCAGCTTCCTCATTGATGGTTTTGTCACT TCCCCTTGGATC | Inner primers using target sites with 22 nt distance | 11 |
| FI primer | ATCAAGCAGCCATGCAAAT | Only "pairing-priming" DAMP | 12 |
| RI primer | AGTTCCTGCTATGTCACTT | Only "pairing-priming" DAMP | 13 |
| F3 primer | ATTATCAGAAGGAGCCACC | LAMP using the same amplification region | 14 |
| B3 primer | GGGATAGGTGGATTACTTGT | LAMP using the same amplification region | 15 |

TABLE 1-continued

LIST OF SEQUENCE INFORMATION OF THE PRIMERS AND TARGETS

| Item | Sequence (5'-3') | Description | SEQ ID NO: |
|---|---|---|---|
| FIP primer | TCTGCAGCTTCCTCATTGATGGTTTTACCATGCTAAACACAGTGG | LAMP using the same amplification region | 16 |
| BIP primer | TTGCACCAGGCCAGATAAGATTTTCCTATTTGTTCCTGAAGGGTAC | LAMP using the same amplification region | 17 |
| LoopF primer | ATTTGCATGGCTGCTTGATGTC | LAMP using the same amplification region | 18 |
| LoopB primer | GAAGTGACATAGCAGGAACTACCA | LAMP using the same amplification region | 19 |
| Swarm primer 1 | TCTGCAGCTTCCTCATTGATGG | Swarm primer added to the LAMP above | 20 |
| Swarm primer 2 | TTGCACCAGGCCAGATAAGA | Swarm primer added to the LAMP above | 21 |
| F primer | ATTATCAGAAGGAGCCACC | PCR | 22 |
| B primer | CATCCTATTTGTTCCTGAAGG | PCR | 23 |
| For the amplification of *E. coli* B malB gene sequence | | | |
| The 300-bp *E. coli* B malB gene sequence inserted into the pUCIDT (Amp) plasmid | GCCAGGGGGTGGAGGATTTAAGCCATCTCCTGATGACGCATAGTCAGCCCATCATGAATGTTGCTGTCGATGACAGGTTGTTACAAAGGGAGAAGGGCATGGCGAGCGTACAGCTGCAAAATGTAACGAAAGCCTGGGGCGAGGTCGTGGTATCGAAAGATATCAATCTCGATATCCATGAAGGTGAATTCGTGGTGTTTGTCGGACCGTCTGGCTGCGGTAAATCGACTTTACTGCGCATGATTGCCGGGCTTGAGACGATCACCAGCGGCGACCTGTTCATCGGTGAGAAACGGATGA | | 24 |
| FO primer | GCTGTCGATGACAGGTTGTT | DAMP | 25 |
| RO primer | ATTTACCGCAGCCAGACG | DAMP | 26 |
| FI primer | TTTTGCAGCTGTACGCTCGTTTTCAAAGGGAGAAGGGCATGG | DAMP | 27 |
| RI Primer | ATCAATCTCGATATCCATGAAGGTGTTTTTCCGACAAACACCACGAATT | DAMP | 28 |
| FC primer | TTTTGCAGCTGTACGCTCG | DAMP | 29 |
| RC primer | ATCAATCTCGATATCCATGAAGGTG | DAMP | 30 |
| F3 primer | GCCATCTCCTGATGACGC | The reported LAMP[1] | 31 |
| B3 primer | ATTTACCGCAGCCAGACG | The reported LAMP[1] | 32 |
| FIP primer | CATTTTGCAGCTGTACGCTCGCAGCCCATCATGAATGTTGCT | The reported LAMP[1] | 33 |
| BIP primer | CTGGGGCGAGGTCGTGGTATTCCGACAAACACCACGAATT | The reported LAMP[1] | 34 |
| LoopF primer | CTTTGTAACAACCTGTCATCGACA | The reported LAMP[1] | 35 |

TABLE 1-continued

LIST OF SEQUENCE INFORMATION OF THE PRIMERS AND TARGETS

| Item | Sequence (5'-3') | Description | SEQ ID NO: |
|---|---|---|---|
| LoopB primer | ATCAATCTCGATATCCATGAAGGTG | The reported LAMP[1] | 36 |
| F primer | GCCATCTCCTGATGACGC | PCR | 37 |
| B primer | ATTTACCGCAGCCAGACG | PCR | 38 |

Reaction Condition and Product Analysis

The real-time fluorescence detection of DAMP and LAMP was performed in the CFX96 Touch™ Real-Time PCR Detection System (Bio-Rad) by incubating the reactions at 60°C for 60 min or 120 min, followed by heating at 80° C. for 20 min. The threshold-time of our DAMP and LAMP assay was defined as the maximum of the second derivative from the fluorescence curve. The data analysis was accomplished by using the Prism 8 (GraphPad Software, GSL Biotech LLC, San Diego, CA). The amplified products were analyzed through the electrophoresis in a 3.0% agarose gel (1×TAE) stained with 1× EvaGreen®.

RESULTS AND DISCUSSION

Principle of the Damp Assay

FIG. 1 illustrates the principle of the DAMP assay. As shown in FIG. 1A, the DAMP assay employs six primers: i) two outer primers (FO and RO), ii) two inner primers (FI and RI), and iii) two pairing-competition primers (FC and RC). Unlike conventional six-primer LAMP assay targeting eight distinct sites (FIG. 7), the six primers of the DAMP recognize six distinct sites of the target DNA sequences which contain: i) F1, R2, R3 sites on the forward target sequence, and ii) F3c, F2c, R1c sites on the reverse sequence. F and R stand for the "forward" and "reverse" directions, respectively. The sites with lowercase "c" represent "complementary" sites. Compared to conventional LAMP primers design (FIG. 7A), the DAMP method has two distinct features (FIG. 1A): i) each inner primer is designed to recognize two target sites with the distance of below 40 nt, which ensures efficient "dual-priming" extension. In addition, a four-thymine oligonucleotide spacer (TTTT spacer) is introduced into the inner primers. However, in the LAMP method, the distance between two target sites of the inner primers is recommended to be 40-60 nt to ensure efficient "self-priming" extension according to the LAMP primer design guide, and ii) two pairing-competition primers are added to initiate the "dual-priming" extension and accelerate the amplification. Interestingly, the addition of the pairing-competition primers does not increase the total number of target sites because their sequences are the same as the 5'-parts of the inner primers (FI/RI). The length and melting temperature ($T_m$) for each site are summarized in FIG. 8. To facilitate the primers design, an online software was developed by using Python.

The DAMP assay typically contains two steps: i) basic structure producing step (FIG. 1B) and ii) cycling amplification step (FIG. 1C and FIG. 9). The reverse target sequence was used as an example to facilitate the explanation of the DAMP amplification mechanism. In the DAMP assay, DNA synthesis is initiated by DNA polymerase when the F2 region of FI primer anneals to the F2c site and the FO primer anneals to the F3c site. Due to the strand-displacement activity of the DNA polymerase, the strand elongated from FI primer is displaced and released by the FO primer extension. Then, the R2 and R3 sites in the released strand are recognized by the RI and RO primers, respectively. Afterwards, the extended strand by RI primer is displaced by the elongated strand from the RO primer. Since the RI primer contains two target sites with a distance of less than 40 nt, the "self-priming" strand extension capability in Basic Structure 1 is reduced compared to the dumb-bell structure in the conventional LAMP method (FIG. 7). Furthermore, due to the addition of pairing-competition primers, the "self-priming" extension (Item 1 in the black box in FIG. 1C) will fully compete with three "pairing-priming" extension events: i) the first "pairing-priming" extension is initiated by the annealing of the F2 site in the FI primer to the F2c site (Item 2 in the box), ii) the second one results from the annealing competition of FC primer to the FI site (Item 3 in the box), and iii) the third one is the concurrence of two aforementioned events (Item 4 in the box). The "self-priming" extension can produce double-stranded DNA (dsDNA) fragments with a closed loop which can be recognized by the FI primer. Then, the "self-priming" and "pairing-priming" strand extensions take place at their 3'-end parts again, and the amplification proceeds to Pathway 1. Unlike the "self-priming" extension, the "pairing-priming" extension can simultaneously generate multiple basic structures for cycling amplification, including duplex basic structure and complementary basic structure (Basic Structure 2 in FIG. 1C). Similarly, "self-priming" and "pairing-priming" extensions occur at both ends of the duplex basic structure, then stepping into Pathways 1 and 2. Whereas, for Basic Structure 2, the "dual-priming" extension occurs only at the 3'-end part, and then moves into the Pathway 2. In the Pathways 1 and 2, owing to the co-mediation effect of "self-priming" and "pairing-priming" extensions, the Basic Structure 1 and 2 are generated again to recycle the amplification. Details on these two pathways are shown in FIG. 9.

Dual-Priming Extension Effect of the Damp Assay

To investigate the "dual-priming" extension mechanism of the DAMP assay, three sets of DAMP primers were designed and tested for HIV-1 p24 gene detection, which contained the same outer and pairing-competition primers but different inner primers with various distances between two target sites (from 5'-end of F2 to 5'-end of F1 and from 3'-end of R1 to 5'-end of R2) in the target sequences (FIG. 2). DAMP inner primers were first designed by setting the distance of their two target sites to be 55 and 56 nt (FIG. 2A, Left) and performed real-time DAMP. As shown in FIG. 2A, Right, it showed low amplification efficiency and obvious nonspecific amplification with elevated baselines. The low amplification efficiency may be attributed to dominant "self-priming" strand extension like the conventional four-primer LAMP. The undesirable nonspecific amplification signals could likely be caused by the formation of primer dimer (FIG. 10A). After reducing the distance to less than 40 nt (e.g., 30 nt), both "self-priming" and "pairing-priming" strand extensions were fully initiated and fairly competed with each other in the DAMP amplification. Such "dual-priming" effect produced more basic structures to mediate downstream cycling amplifications, enabling high efficiency DAMP amplification reaction with ultralow nonspecific signals (FIG. 2B). However, upon further reducing the distance (e.g., 22 nt) (FIG. 2C), the "self-priming" extension capability is dramatically suppressed, which influenced the formation of basic products and resulted in a low amplification efficiency. To further confirm this, their DAMP products were subjected to gel electrophoresis (FIG. 10). Therefore, these results demonstrated that the optimization of the distance was necessary to design efficient primers for highly sensitive DAMP assay.

To further confirm that "dual-priming" extension is crucial in our DAMP assay, the effect of single "self-priming" and single "pairing-priming" extension on isothermal amplification was also investigated by fixing the distance of two target sites at 30 nt for the inner primer design. First, the F1c and RI region were respectively deleted from the FI and RI primers only to initiate single "pairing-priming" strand extension (FIG. 11A, Left). As shown in FIG. 11A, Right, the amplification efficiency of such single "pairing-priming" extension was very low. Next, we did not add the pairing-competition primers (FC/RC) to initiate single "self-priming" extension (FIG. 11B, Left). As shown in FIG. 11B, Right, single "self-priming" extension had lower amplification efficiency with increased detection time compared to the "dual-priming" extension (FIG. 11C). Therefore, the results demonstrate that the "dual-priming" extension effect plays a critical role in achieving highly efficient and fast nucleic acid isothermal amplification in our DAMP assay.

Optimization of the Damp Assay

To achieve a highly sensitive detection of nucleic acids, the DAMP reaction was first optimized by investigating the effect of the concentration of various composites (e.g., DNA polymerase, dNTPs, betaine, and $MgSO_4$). To investigate the DNA polymerase's effect, the concentration of DNA polymerase was increased from 0.16 U/µL to 1.2 U/µL. As shown in FIG. 3A, the higher the DNA polymerase concentrations was, the faster the amplification was as well. Herein, 1.2 U/µL DNA polymerase was used as the optimal concentration because of its fastest speed. It should be mentioned that the increasing polymerase amount did not cause false positive signal in this DAMP assay (FIG. 12) unlike the conventional LAMP assay (typically 0.32 U/µL polymerase).

Figure 13:
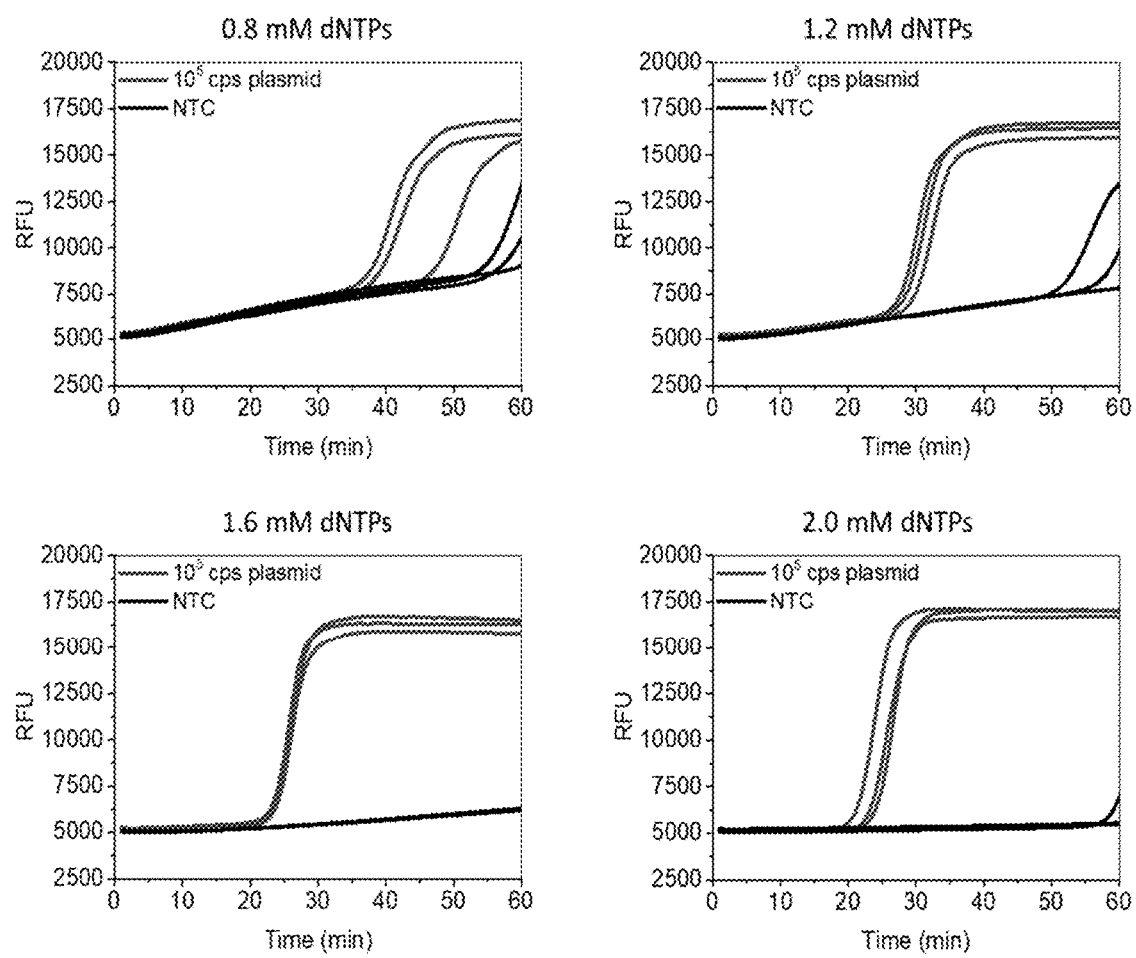
FIG. 13 shows real-time fluorescence signals of DAMP assay using various concentrations of dNTPs. The 300-bp HIV-1 p24 gene cDNA sequence inserted into a plasmid was the target sequence. Positive, three replicated reactions with 105 copies templates. NTC, three replicated non-template control reactions.
Figure 14:
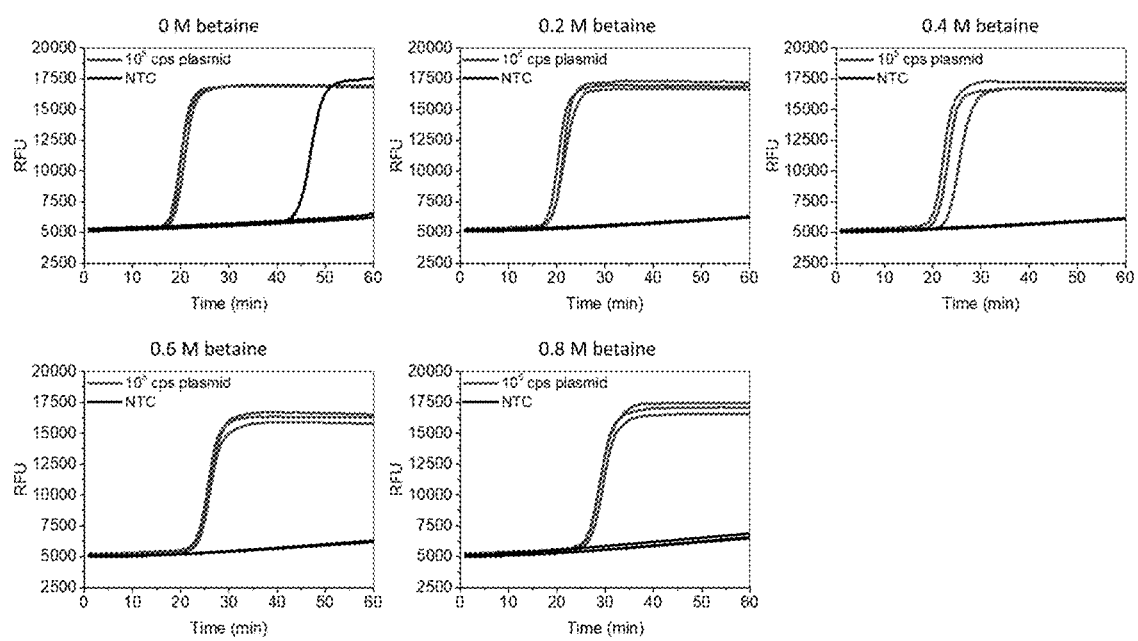
FIG. 14 shows real-time fluorescence signals of DAMP assay using various concentrations of betaine. The 300-bp HIV-1 p24 gene cDNA sequence inserted into a plasmid was the target sequence. Positive, three replicated reactions with $10^5$ copies templates. NTC, three replicated non-template control reactions.
Figure 15:
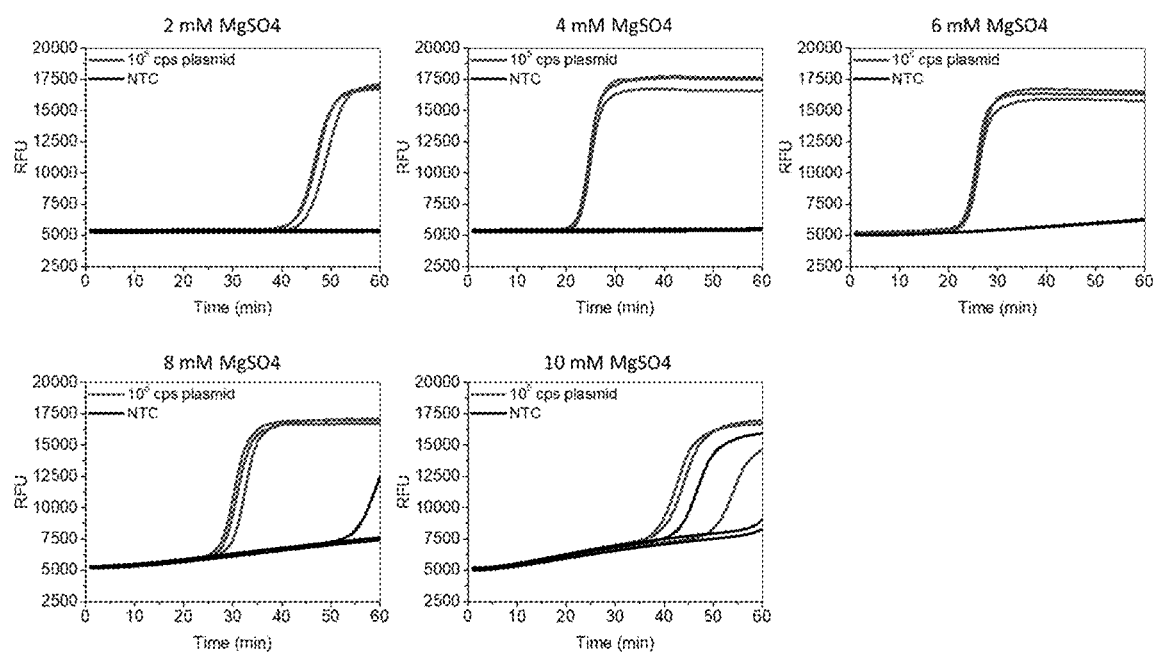
FIG. 15 shows real-time fluorescence signals of DAMP assay using various concentrations of $MgSO_4$. The 300-bp HIV-1 p24 gene cDNA sequence inserted into a plasmid was the target sequence. Positive, three replicated reactions with $10^5$ copies templates. NTC, three replicated non-template control reactions.
Figure 16:
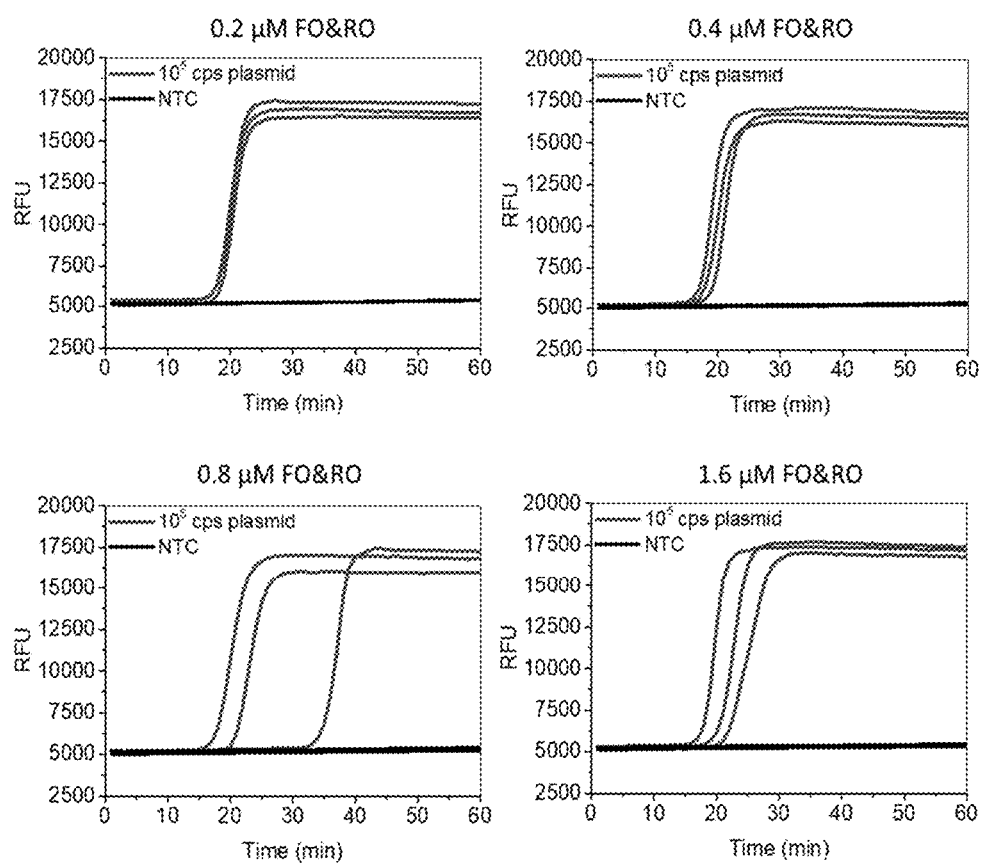
FIG. 16 shows real-time fluorescence signals of DAMP assay using various concentrations of outer primers FO and RO. The 300-bp HIV-1 p24 gene cDNA sequence inserted into a plasmid was the target sequence. Positive, three replicated reactions with $10^5$ copies templates. NTC, three replicated non-template control reactions.
Figure 17:
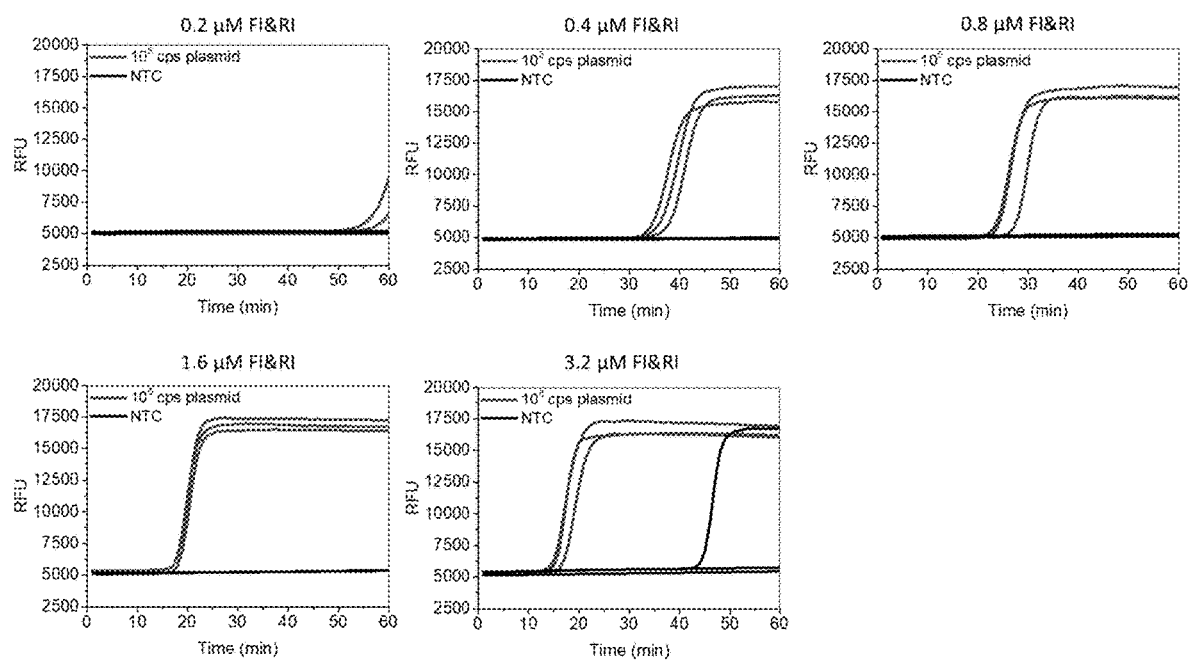
FIG. 17 shows real-time fluorescence signals of DAMP assay using various concentrations of inner primers FI and RI. The 300-bp HIV-1 p24 gene cDNA sequence inserted into a plasmid was the target sequence. Positive, three replicated reactions with $10^5$ copies templates. NTC, three replicated non-template control reactions.
Figure 18:
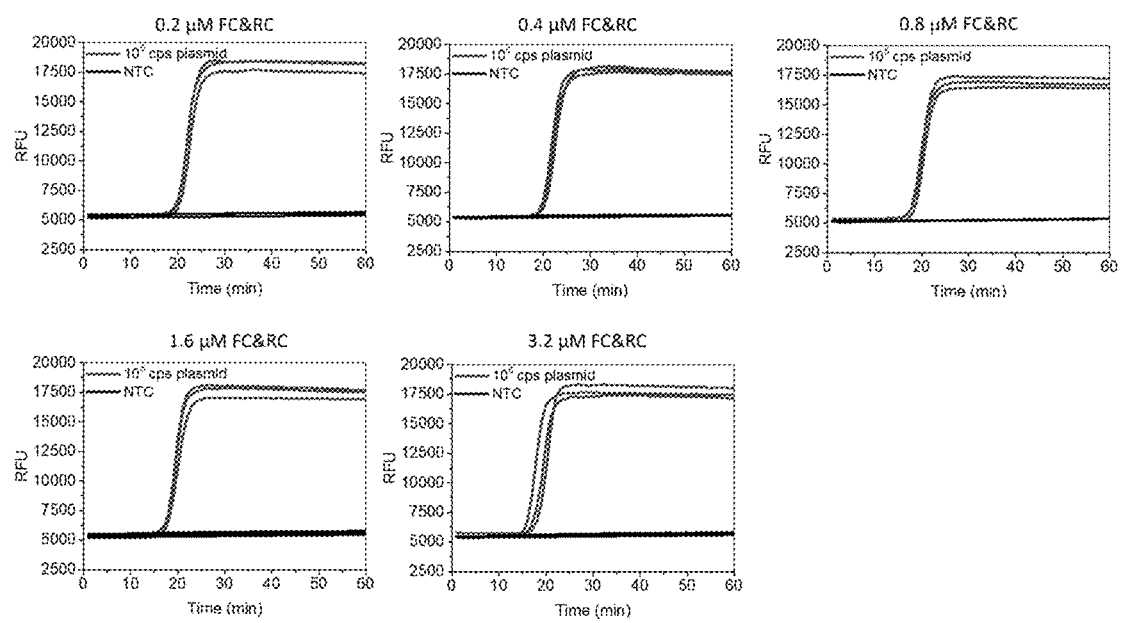
FIG. 18 shows real-time fluorescence signals of DAMP assay using various concentrations of pairing-competition primers FC and RC. The 300-bp HIV-1 p24 gene cDNA sequence inserted into a plasmid was the target sequence. Positive, three replicated reactions with $10^5$ copies templates. NTC, three replicated non-template control reactions.

Then, the effect of dNTPs, betaine, and $MgSO_4$ on the DAMP assay were investigated. During the nucleic acid amplification, the dNTPs are essential to build blocks of nucleic acid molecules. With the increase of dNTPs concentration, the threshold time became shorter (FIG. 3B). To ensure highly specific isothermal amplification, 1.6 mM dNTPs was chosen in our DAMP assay (FIG. 3B and FIG. 13). Betaine is often used as an isostabilizing additive of isothermal amplification reactions to reduce dsDNA's $T_m$ and facilitate the strand separation. In this DAMP assay, 0.2 M betaine was optimal because it provided the fastest amplification speed with high specificity (FIG. 3C and FIG. 14). Magnesium ions have been known to act as cofactor of DNA polymerase. Thus, various concentrations of magnesium ions were assessed in the DAMP assay. As shown in FIG. 3D and FIG. 15, when using 4 mM $MgSO_4$, DAMP amplification could be achieved within the shortest time and did not result in nonspecific amplification.

Next, the concentrations of primers were investigated and optimized. As shown in FIGS. 4A-4C and FIGS. 16-18, the optimal concentrations of FO & RO, FI & RI, and FC & RC were 0.2 µM, 1.6 µM, and 1.6 µM, respectively. Thus, the optimized DAMP reaction solution contains 1.2 U/µL polymerase, 1.6 mM each of dNTPs, 0.2 M betaine, 4 mM $MgSO_4$, 0.2 µM FO & RO, 1.6 µM FI & RI, and 1.6 µM FC & RC. With the optimized DAMP assay, HIV-1 DNA could be rapidly detected with ultralow nonspecific signal (FIG. 4D).

Nonspecific Amplification Evaluation of the Damp Assay

To evaluate the ultralow nonspecific amplification of our DAMP assay, both six-primer LAMP and DAMP assay were designed and tested by targeting the same DNA sequence (FIG. 5A, Left and FIG. 5B, Left). As shown in FIG. 5A, Right, obviously ascended baselines were observed for NTC in the six-primer LAMP assay, which was caused by the formation of primer dimers. On the contrary, the DAMP assay had significantly lower initial background baseline signal (FIG. 5B, Right). To further confirm that the rising baseline of the six-primer LAMP assay originated from the primer dimers, the amplification products of both DAMP and LAMP assays were subject to gel electrophoresis analysis. As shown in FIG. 5B, nonspecific amplicon band was clearly observed in the NTC of the six-primer LAMP assay but not seen in the DAMP's NTC. In addition, melting curve analysis results further confirmed that the nonspecific amplification was observed only in the six-primer LAMP assay (FIG. 19). Due to the ultralow nonspecific amplification, the endpoint fluorescence difference between positive and negative products of the DAMP assay was at least twice as high as that of the six-primer LAMP (FIG. 5D). That is beneficial for many microfluidic-based point-of-care molecular detection. Compared to the six-primer LAMP, DAMP assay showed higher amplification yield (FIG. 5D) and faster reaction speed (FIG. 20). That could be possibly attributed to extra cycling amplifications resulting from multiple basic structures produced by "dual-priming" extension in the DAMP assay.

Furthermore, the performance of this DAMP assay was compared to other LAMP variants (FIG. 21): i) four-primer LAMP (without two loop primers), ii) four-primer LAMP with two swarm primers, and iii) six-primer LAMP with the swarm primers. In order to ensure reliable comparison, the primers of these LAMP variants were designed based on the same target sequence as the DAMP method. As shown in FIG. 21, all three LAMP variants showed stronger nonspecific amplification signals with rising background curves compared to the DAMP method. Further, extended reaction times were examined to determine whether this could lead to false positive signals caused by nonspecific exponential amplification. As shown in FIG. 22A, false-positive signals were not observed for the NTC in the DAMP assay even after 120-min incubation but present in six-primer LAMP's NTC (FIG. 22B). As a result, the DAMP assay provided ultralow nonspecific amplification and enabled highly sensitive and specific nucleic acid detection.

Analytical Performance of the Damp Assay

To determine the sensitivity of the DAMP assay, different plasmid HIV-1 DNA targets ranging from 101 to 107 copies/µL were detected. As shown in FIG. 6A, this DAMP assay could detect 100 copies HIV DNA per reaction, which is equal to or better than that of the six-primer LAMP (FIG. 23A and FIG. 24A) and the real-time PCR method (FIG. 23B).

Furthermore, due to higher amplification efficiency, the DAMP assay showed shorter threshold time compared to that of LAMP assay (FIG. 6B and FIG. 24). In addition, to demonstrate the feasibility of our DAMP assay for RNA detection, the HIV-1 RNA was detected using reverse transcription DAMP (RT-DAMP). HIV-1 RNA was extracted from inactivated HIV virus in plasma (AcroMetrix™ HIV-1 High Control, Thermo Fisher Scientific). As shown in FIG. 6C and FIG. 25, RT-DAMP was able to consistently detect 350 copies for HIV-1 RNA target with ultralow specificity and faster amplification, compared to six-primer RT-LAMP (FIG. 6D).

Figure 26:
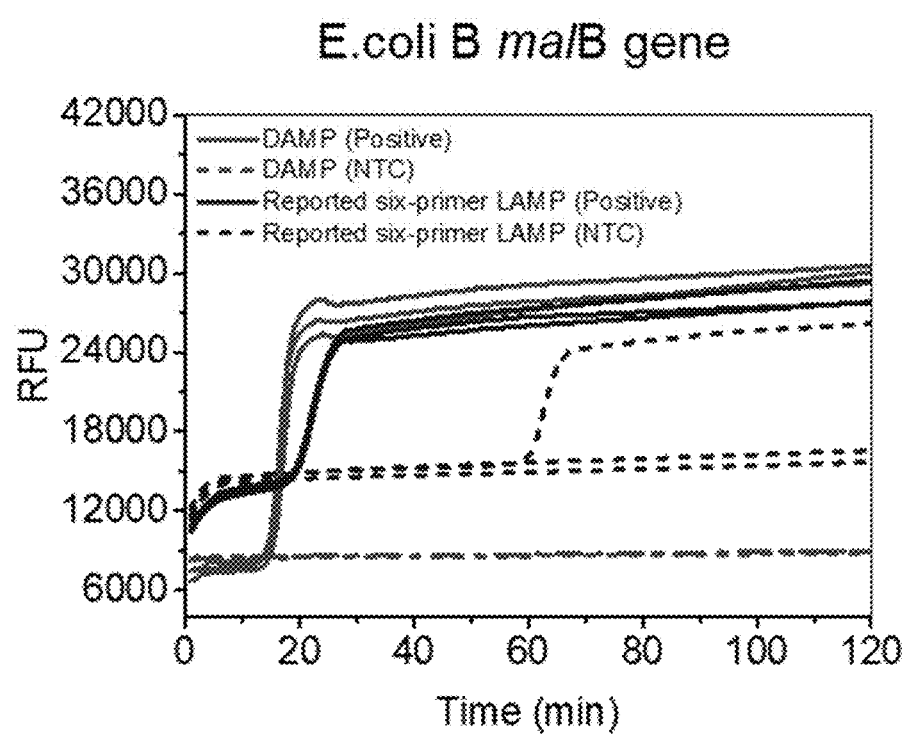
FIG. 26 shows real-time fluorescence signals of DAMP and the reported six-primer LAMP for the amplification of E. coli B malB gene sequences within two-hour incubation. Positive, three replicated reactions with $10^5$ copies templates are shown.

To evaluate the versatility of this DAMP assay, this DAMP method was applied to detect E. coli B malB gene and its performance was compared with the previously published six-primer LAMP assay. As shown in FIG. 6E, DAMP assay could achieve a sensitivity of 100 copies per reaction, which was comparable to those of LAMP assay (FIG. 23C) and the real-time PCR method (FIG. 23D). However, compared to the LAMP assay, DAMP showed faster amplification speed (FIG. 6F and FIG. 24). Similar to the above-mentioned HIV DNA detection, the DAMP assay for E. coli DNA had ultralow background fluorescence signals and did not show false-positive results after 120-min incubation (FIG. 26). Collectively, all these data showed that DAMP assay was a rapid, versatile, sensitive isothermal amplification method with ultralow nonspecific signal.

CONCLUSION

Compared to the conventional LAMP assay, the DAMP method developed in this example offers several advantages, including: i) ultralow nonspecific signal. DAMP showed an ultralow nonspecific signal even after two-hour incubation due to the unique inner primer design and the addition of two pairing-competition primers. ii) Shorter amplification time. The DAMP assay had higher amplification efficiency with shorter detection time because of its "dual-priming" strand extension mechanism that could simultaneously generate multiple basic structures for cycling amplification. iii) Simpler primer design. Unlike conventional six-primer LAMP, the six-primers of our DAMP assay only recognized six sites, which simplified the complexity of primer design and reduced the potential risk of forming false-positive. In addition, the DAMP assay was shown to be versatile for detection of various nucleic acid targets. Therefore, the DAMP assay described here has great potential for infectious disease diagnostics, food safety monitoring, and cancer early screening as a point of care testing, particularly in resource-limited clinical settings. apid nucleic acid detection.

We claim:

1. A method of amplifying a target nucleic acid, comprising contacting a nucleic acid sample suspected of containing the target nucleic acid with six primers and a DNA polymerase with strand displacement activity, wherein
the target nucleic acid comprises from 5' to 3', an F3 site, an F2 site, an F1 site, an R1 site, an R2 site, and an R3 site, and the complement to the target nucleic acid comprises, from 3' to 5', an F3c site, an F2c site, an F1c site, an R1c site, an R2c site, and an R3c site, and
the six primers comprise
a forward outer primer (FO) complementary to the F3c site,
a reverse outer primer (RO) complementary to the R3 site,
a forward inner primer (FI) comprising the F1c and F2 sites,
a reverse inner primer (RI) comprising the R1 and R2c sites,
a forward reverse pairing-competition primer (FC) complementary to the F1 site, and
a reverse pairing-competition primer (RC) complementary to the R1c site,
wherein the forward outer primer (FO), the reverse outer primer (RO), the forward reverse pairing-competition primer (FC), and the reverse pairing-competition primer (RC) are single site primers, and the forward inner primer (FI) and the reverse inner primer (RI) are double site primers; and
amplifying the target nucleic acid with the DNA polymerase, wherein amplifying comprises
producing a first basic structure comprising from 5' to 3', the R1 site, the R2c site, the R1c site, the F1c site, the F2c site, and the F1 site, wherein producing comprises (a) synthesizing DNA from (1) the forward outer primer (FO) annealing to the F3c site with the DNA polymerase and (2) the F2 region of the forward inner primer (FI) annealing to the F2c site with the DNA polymerase, wherein the strand elongated from the forward inner primer (FI) is displaced and released by the extension from the forward outer primer (FO), and
(b) synthesizing DNA (1) with the DNA polymerase from the reverse outer primer (RO) annealing to the R3 site and (2) with the DNA polymerase from the R2c region of the reverse inner primer (RI) annealing the R2 site of the released nucleic acid strand, wherein the strand elongated from the reverse inner primer (RI) is displaced and released by the extension from the reverse outer primer (RO), thereby producing the first basic structure, and
cyclically amplifying the first basic structure by contacting the first basic structure with the DNA polymerase, the forward inner primer (FI), the reverse pairing-competition primer (RC), the forward reverse pairing-competition primer (FC), and the reverse inner primer (RI) to provide amplified target nucleic acid.

2. The method of claim 1, wherein
the distance from the first nucleotide of the F2 site to the first nucleotide of the FI site in the target nucleic acid sequence is less than 40 nucleotides,
the distance from the first nucleotide of the R2c site to the first nucleotide of the R1c site in the complement to the target nucleic acid sequence is less than 40 nucleotides, or
a combination thereof.

3. The method of claim 1, wherein the cyclic amplifying comprises
- (A) synthesizing DNA (1) with the DNA polymerase from the annealing of the FI site of the first basic structure and the F1c site of the first basic structure and (2) with the DNA polymerase from the F2 region of the forward inner primer (FI) annealing to the F2c site of the first basic structure,
- (B) synthesizing DNA with the DNA polymerase from the forward reverse pairing-competition primer (FC) annealing to the FI site of the first basic structure with the DNA polymerase, thereby producing a duplex basic structure comprising a first basic structure and a second basic structure, the second basic structure from 5' to 3', the F1c site, the F2 site, the F1 site, the RI site, the F2 site, and the R1c site, or
- (C) synthesizing DNA (1) with the DNA polymerase from the annealing of the F2 region of the forward inner primer (FI) annealing to the F2c site of the first basic structure and (2) with the DNA polymerase from the forward reverse pairing-competition primer (FC) annealing to the F1 site of the first basic structure, wherein the strand elongated from the forward inner primer (FI) is displaced and released by the extension from the forward reverse pairing-competition primer (FC), thereby producing a duplex basic structure and a second basic structure, or
- (D) a combination thereof.

4. The method of claim 3, wherein the cyclic amplifying further comprises
- (1) synthesizing DNA (i) with the DNA polymerase from the annealing of the F2 region of the forward inner primer (FI) annealing to the F2c site of the first basic structure of the duplex basic structure and (ii) with the DNA polymerase from the forward reverse pairing-competition primer (FC) annealing to the FI site of the first basic structure of the duplex basic structure of (B) or (C), wherein the strand elongated from the forward inner primer (FI) is displaced and released by the extension from the forward reverse pairing-competition primer (FC), thereby producing a duplex basic structure and a second basic structure,
- (2) synthesizing DNA (i) with the DNA polymerase from the annealing of the R2c region of the reverse inner primer (RI) annealing to the R2 site of the second basic structure or the second basic structure of the basic duplex structure from (B) or (C) and (ii) with the DNA polymerase from the reverse pairing-competition primer (RC) annealing to the R1C site of the second basic structure or the second basic structure of the basic duplex structure from (B) or (C), wherein the strand elongated from the reverse inner primer (RI) is displaced and released by the extension from the reverse pairing-competition primer (RC), thereby a the duplex basic structure and a first basic structure,
- (3) synthesizing DNA (i) with the DNA polymerase from the R2c region of the reverse inner primer (RI) annealing to the R2 site of the product of (A) and (ii) with the DNA polymerase from the reverse pairing-competition primer (RC) annealing to the R1C site of the product of (A), wherein the strand elongated from the reverse inner primer (RI) is displaced and released by the extension from the reverse pairing-competition primer (RC), or
- (4) a combination thereof.

5. The method of claim 1, wherein the F1c site and the F2 site of the forward inner primer (FI) are separated by a TTTT spacer.

6. The method of claim 1, wherein the R1 site and the R2c site of the reverse inner primer (RI) are separated by a TTTT spacer.

* * * * *